United States Patent
Sawada et al.

(10) Patent No.: US 10,695,015 B2
(45) Date of Patent: Jun. 30, 2020

(54) SOLID-STATE IMAGE CAPTURING DEVICE, RADIATION IMAGE CAPTURING SYSTEM, AND METHOD OF CONTROLLING SOLID-STATE IMAGE CAPTURING DEVICE

(71) Applicant: HAMAMATSU PHOTONICS K.K., Hamamatsu-shi, Shizuoka (JP)

(72) Inventors: Junichi Sawada, Hamamatsu (JP); Ryuji Kyushima, Hamamatsu (JP); Haruyoshi Okada, Hamamatsu (JP); Kazuki Fujita, Hamamatsu (JP); Harumichi Mori, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 16/323,527

(22) PCT Filed: Aug. 9, 2017

(86) PCT No.: PCT/JP2017/029000
§ 371 (c)(1),
(2) Date: Feb. 6, 2019

(87) PCT Pub. No.: WO2018/030490
PCT Pub. Date: Feb. 15, 2018

(65) Prior Publication Data
US 2019/0167214 A1  Jun. 6, 2019

(30) Foreign Application Priority Data
Aug. 10, 2016  (JP) .................. 2016-157981

(51) Int. Cl.
*A61B 6/14* (2006.01)
*A61B 6/00* (2006.01)
*G01T 1/24* (2006.01)

(52) U.S. Cl.
CPC .............. *A61B 6/4233* (2013.01); *A61B 6/00* (2013.01); *A61B 6/14* (2013.01); *A61B 6/54* (2013.01); *G01T 1/247* (2013.01); *A61B 6/4452* (2013.01)

(58) Field of Classification Search
CPC ....... A61B 6/14; A61B 6/4233; A61B 6/4452; A61B 6/54; A61B 6/585; G01T 1/247; G01T 1/2928
See application file for complete search history.

(56) References Cited

U.S. PATENT DOCUMENTS 5,138,458 A * 8/1992 Nagasaki ............... H04N 5/335
348/222.1
5,748,307 A * 5/1998 Nakamura ............. H04N 9/735
348/222.1

(Continued)

FOREIGN PATENT DOCUMENTS

EP  2269514 A1  1/2011
JP  H04-144548 A  5/1992

(Continued)

OTHER PUBLICATIONS

International Preliminary Report on Patentability dated Feb. 21, 2019 for PCT/JP2017/029000.

*Primary Examiner* — David P Porta
*Assistant Examiner* — Fani Boosalis
(74) *Attorney, Agent, or Firm* — Faegre Drinker Biddle & Reath LLP

(57) ABSTRACT

The present embodiment relates to a radiation imaging system and the like provided with a solid-state imaging device having a structure enabling reduction of linear noise appearing in an integrated image. The solid-state imaging device comprises: L pieces of imaging pixel region arranged along a direction crossing a moving direction of a relative position of the solid-state imaging device; and L pieces of (Continued)

A/D converter provided corresponding to the L pieces of imaging pixel region. Each imaging pixel region includes pixels arranged two-dimensionally to form an M-row by N-column matrix. Any one of the L pieces of A/D converter executes a dummy A/D conversion once or more times after an A/D conversion of an electric signal from a pixel of an m-th row, before an A/D conversion of an electric signal from a pixel of an (m+1)-th row.

10 Claims, 14 Drawing Sheets

(56) References Cited

U.S. PATENT DOCUMENTS

| | | | |
|---|---|---|---|
| 2013/0136234 A1* | 5/2013 | Noma | H05G 1/64 378/91 |
| 2015/0264281 A1 | 9/2015 | Yoo | |
| 2016/0131772 A1 | 5/2016 | Sato | |

FOREIGN PATENT DOCUMENTS

| | | |
|---|---|---|
| JP | 2004-32212 A | 1/2004 |
| JP | 2006-94108 A | 4/2006 |

* cited by examiner

SOLID-STATE IMAGE CAPTURING DEVICE, RADIATION IMAGE CAPTURING SYSTEM, AND METHOD OF CONTROLLING SOLID-STATE IMAGE CAPTURING DEVICE

TECHNICAL FIELD

The present invention relates to a solid-state imaging device, a radiation imaging system, and a method of controlling a solid-state imaging device.

BACKGROUND ART

Patent Document 1 discloses a technique relating to a digital panorama x-ray imaging device. This device comprises a rotary means, an image storage means, and an image processing means. The rotary means integrally rotates an X-ray source and an X-ray image detection section, which are arranged opposite to each other across a subject, around the subject. The image storage means sequentially stores image information obtained by the X-ray image detection section as a frame image. The image processing means sequentially derives image information from the image storage means at predetermined time intervals, and adds the information of each image while shifting the information of each image by a predetermined distance to form a panoramic image.

CITATION LIST

Patent Literature

Patent Document 1: Japanese Patent Application Laid-Open No. H4-144548

SUMMARY OF INVENTION

Technical Problem

As a result of considering the above-described conventional technique, the inventors have found the following problems. That is, as a radiation imaging system, there is a system to generate an image by repeatedly capturing a radiation image of a subject while relatively moving the subject and a solid-state I imaging device, and integrating a plurality of frame images obtained by repeating the imaging while shifting the frame images along an axial direction corresponding to a moving direction of the solid-state imaging device by a distance corresponding to a moving speed of the solid-state imaging device. For example, a dental X-ray imaging system for acquiring a digital panoramic image of a patient's jaw captures 3000 to 4000 frame images while moving a solid-state imaging device having an elongated light receiving part along a periphery of the jaw in a state where a longitudinal direction of the light receiving part crosses a moving direction of the solid-state imaging device. Then, a clear digital panoramic image can be obtained by integrating these frame images while shifting the frame images by a distance corresponding to a moving speed of the solid-state imaging device in accordance with an axial direction corresponding to a moving direction of the solid-state imaging device.

In the radiation imaging system, the light receiving part of the solid-state imaging device may be divided into a plurality of imaging pixel regions arranged in a longitudinal direction. This is because a readout speed can be increased by reading out pixel data of a plurality of imaging pixel regions in parallel. However, in such a case, pixel values may be discontinuous at a boundary line of the plurality of imaging pixel regions. Furthermore, since an arrangement direction of the plurality of imaging pixel regions crosses a moving direction, the boundary line of the plurality of imaging pixel regions extends along the moving direction. Therefore, pixel data of pixels adjacent to the boundary line is repeatedly integrated, and discontinuity is emphasized. This causes linear noise to appear at the boundary line part of an integrated image.

The present invention has been made to solve the above-mentioned problems, and an object thereof is to provide a solid-state imaging device having a structure for effectively reducing linear noise appearing in an integrated image, a radiation imaging system, and a method of controlling a solid-state imaging device.

Solution to Problem

In order to solve the problems as described above, a radiation imaging system including a solid-state imaging device according to the present embodiment comprises at least a moving mechanism and an image generation unit, in addition to the solid-state imaging device. The solid-state imaging device applicable to the radiation imaging system has L (an integer of 2 or more) pieces of imaging pixel region arranged in a first direction, and captures a radiation image of a subject irradiated with radiation from a radiation source. The moving mechanism relatively moves a position of the solid-state imaging device with respect to the subject along a second direction crossing the first direction. The image generation unit generates an image by integrating each of a plurality of frame images obtained by repeatedly capturing a radiation image of a subject while moving a relative position of the solid-state imaging device with respect to the subject along the second direction, while shifting the frame images along an axial direction corresponding to the second direction by a distance corresponding to a moving speed of the relative position of the solid-state imaging device. In particular, the solid-state imaging device according to the present embodiment comprises at least a light receiving part having L pieces of imaging pixel region, a row selection unit, a column selection unit, L pieces of A/D converter respectively provided corresponding to the L pieces of imaging pixel region, and a control system. Each of the L pieces of imaging pixel region of the light receiving part includes M (an integer of 2 or more)×N (an integer of 2 or more) pieces of pixel arranged two-dimensionally. Further, pixels constituting each column of an M-row by N-column matrix corresponding to the two-dimensional array of M×N pieces of pixel extend along two directions. The row selection unit outputs an electric signal corresponding to a charge quantity generated in each of pixels constituting any one row of the M-row by N-column matrix. The column selection unit outputs an analog signal based on the electric signal outputted from each of pixels constituting a row selected by the row selection unit, to an output wiring for each column of the M-row by N-column matrix. The L pieces of A/D converter convert the analog signal transmitted via the output wiring into a digital signal constituting a frame image. The control system at least gives an instruction on an operation timing of an A/D conversion in each of the L pieces of A/D converter. Specifically, during a period of acquiring at least one specific frame image among a plurality of frame images obtained by repeatedly capturing a radiation image of a subject, the control system outputs an A/D conversion control signal once or more times for causing at least any A/D converter selected from among the L pieces of A/D converter to execute a dummy A/D conversion, after the selected A/D converter converts analog signals from pixels constituting an m-th row (an integer of 1 or more and M or less) out of the M-row by N-column matrix into digital signals, and before converting analog signals from pixels constituting an (m+1)-th row into digital signals.

In addition, a method of controlling a solid-state imaging device according to the present embodiment is directed to a solid-state imaging device having the above-described structure. Specifically, this controlling method comprises a first A/D conversion step, a second A/D conversion step, and a dummy A/D conversion step. In the first A/D conversion step, analog signals based on electric signals from pixels constituting an m-th row of the M-row by N-column matrix are converted into digital signals for each column of the m-th row in the L pieces of A/D converter. In the second A/D conversion step, analog signals based on electric signals from pixels constituting an (m+1)-th row of the M-row by N-column matrix are converted into digital signals for each column of the (m+1)-th row in the L pieces of A/D converter. In the dummy A/D conversion step, during a period of acquiring at least any frame image among a plurality of frame images, at least any A/D converter among the L pieces of A/D converter executes a dummy A/D conversion once or more times between the first A/D conversion step and the second A/D conversion step.

Advantageous Effects of Invention

According to the solid-state imaging device, the radiation imaging system, and the method of controlling the solid-state imaging device according to the present embodiment, it is possible to reduce linear noise appearing in an integrated image.

DESCRIPTION OF EMBODIMENTS

Description of Embodiment of Present Invention

Figure 1:
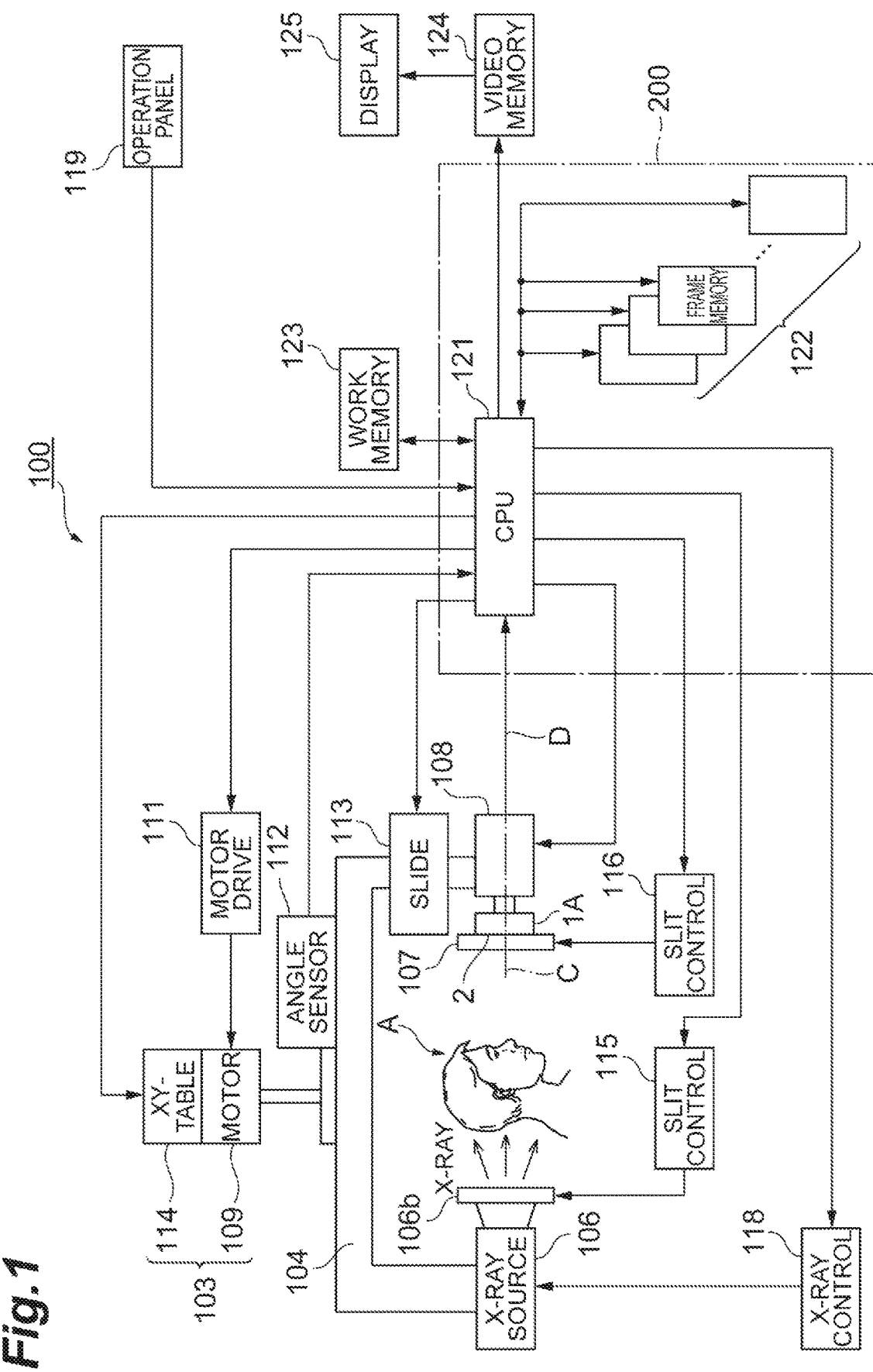
FIG. 1 is a diagram showing a configuration of a medical X-ray imaging system as an example of a radiation i imaging system according to the present embodiment.

First, contents of an embodiment of the present invention will be individually listed and described.

(1) A radiation imaging system including a solid-state imaging device according to the present embodiment comprises, as one aspect thereof, at least a moving mechanism and an image generation unit, in addition to the solid-state imaging device. The solid-state imaging device applicable to the radiation imaging system has L (an integer of 2 or more) pieces of imaging pixel region arranged in a first direction, and captures a radiation image of a subject irradiated with radiation from a radiation source. The moving mechanism relatively moves a position of the solid-state imaging device with respect to the subject along a second direction crossing the first direction. The image generation unit generates an image by integrating each of a plurality of frame images obtained by repeatedly capturing a radiation image of a subject while moving a relative position of the solid-state imaging device with respect to the subject along the second direction, while shifting the frame images along an axial direction corresponding to the second direction by a distance corresponding to a moving speed of the relative position of the solid-state imaging device.

In particular, the solid-state imaging device according to the present embodiment comprises, as one aspect thereof: at least, a light receiving part having L pieces of imaging pixel region; a row selection unit; a column selection unit; L pieces of A/D converter respectively provided corresponding to the L pieces of imaging pixel region; and a control system. Each of the L pieces of imaging pixel region of the light receiving part includes M (an integer of 2 or more)×N (an integer of 2 or more) pieces of pixel arranged two-dimensionally. Further, pixels constituting each column of an M-row by N-column matrix corresponding to the two-dimensional array of M×N pieces of pixel extend along two directions. The row selection unit outputs an electric signal corresponding to a charge quantity generated in each of pixels constituting any one row of the M-row by N-column matrix. The column selection unit outputs an analog signal based on the electric signal outputted from each of pixels constituting a row selected by the row selection unit, to an output wiring for each column of the M-row by N-column matrix. The L pieces of A/D converter convert the analog signal transmitted via the output wiring into a digital signal constituting a frame image. The control system at least gives an instruction on an operation timing of an A/D conversion in each of the L pieces of A/D converter. Specifically, during a period of acquiring at least one specific frame image among a plurality of frame images obtained by repeatedly capturing a radiation image of a subject, the control system outputs an A/D conversion control signal once or more times for causing at least any A/D converter selected from among the L pieces of A/D converter to execute a dummy A/D conversion, after the selected A/D converter converts analog signals from pixels constituting an m-th row (an integer of 1 or more and M or less) out of the M-row by N-column matrix into digital signals, and before converting analog signals from pixels constituting an (m+1)-th row into digital signals.

(2) In addition, a method of controlling a solid-state imaging device according to the present embodiment is directed to a solid-state imaging device having the above-described structure according to the present embodiment. Specifically, the method of controlling a solid-state imaging device comprises, as one aspect thereof, a first A/D conversion step, a second A/D conversion step, and a dummy A/D conversion step. In the first A/D conversion step, analog signals based on electric signals from pixels constituting an m-th row of the M-row by N-column matrix are converted into digital signals for each column of the m-th row in the L pieces of A/D converter. In the second A/D conversion step, analog signals based on electric signals from pixels constituting an (m+1)-th row of the M-row by N-column matrix are converted into digital signals for each column of the (m+1)-th row in the L pieces of A/D converter. In the dummy A/D conversion step, during a period of acquiring at least any frame image among a plurality of frame images, at least any A/D converter among the L pieces of A/D converter executes a dummy A/D conversion once or more times between the first A/D conversion step and the second A/D conversion step.

When pixel data of the plurality of imaging pixel regions are read out in parallel, an A/D converter may be provided in each imaging pixel region. In that case, the following operation is performed in parallel in each imaging pixel region. First, an electric signal (e.g., charge or voltage signal) corresponding to a charge quantity generated in each pixel of a first row is outputted. The row selection unit controls this output timing. Next, an analog signal based on this electric signal is outputted to the output wiring for each column. The outputted analog signal is A/D-converted for each column by the A/D converter, and a digital signal A/D-converted from the analog signal is outputted to outside the solid-state imaging device. Such an operation is also performed sequentially for each of second and subsequent rows.

The inventors have found that a cause of discontinuity of pixel values at a boundary line between a plurality of imaging pixel regions is attributed to an output characteristic of the A/D converter. That is, after sequentially converting analog signals from a first column to a last column of a certain row into digital signals, the A/D converter sequentially converts analog signals from a first column to a last column of the next row into digital signals. At that time, in the A/D converter, when starting a conversion of the next row after completion of conversion of the certain row, the output characteristic of the first one or several times of A/D conversion may be different from usual (may become unstable). Therefore, a discontinuity occurs between pixel data of a pixel on one side (that is, a pixel of the last column) and pixel data of a pixel on the other side (that is, a pixel of the first column) among pixels located on both sides of the boundary line between the imaging pixel regions.

(3) Therefore, in the radiation imaging system and the method of controlling the solid-state imaging device according to the present embodiment, as one aspect thereof, during a period of acquiring at least one specific frame image among a plurality of frame images obtained by the solid-state imaging device, the control system outputs an instruction (A/D conversion control signal) to at least any A/D converter among the L pieces of A/D converter to execute a dummy A/D conversion once or more times, after an A/D conversion of an m-th row (after the first A/D conversion step), before an A/D conversion of an (m+1)-th row (before the second A/D conversion step). Note that, in this specification, the dummy A/D conversion is an A/D conversion executed during a period where the A/D converter is not receiving a significant analog signal. This can suppress a change in the output characteristic of the first one or several times of A/D conversion in starting the A/D conversion of the next row after completion of an A/D conversion of a certain row. That is, discontinuity of pixel values at the boundary line between the plurality of imaging pixel regions is reduced. Therefore, according to the radiation imaging system and the method of controlling the solid-state imaging device, linear noise appearing in an integrated image can be effectively reduced.

(4) As one aspect of the present embodiment, the solid-state imaging device may comprise a hold circuit arranged between the light receiving part and the output wiring. This hold circuit holds an analog signal before being outputted to the output wiring for each column. Meanwhile, the A/D converter selected by the control system may perform a dummy A/D conversion after the hold circuit takes in the analog signal. This can avoid superimposition of noise caused by the operation of the A/D converter on an analog signal when the analog signal is held by the hold circuit.

(5) Further, as one aspect of the present embodiment, during a period of acquiring one specific frame image among a plurality of frame images, the control system may cause all of the L pieces of A/D converter to execute a dummy A/D conversion. Alternatively, as one aspect of the present embodiment, the control system may cause some A/D converters (L1 pieces of A/D converter) among the L pieces of A/D converter to execute a dummy A/D conversion. Note that L1 is an integer of 2 or more and L or less. The effects of the radiation imaging system as described above can be suitably exhibited in any of these aspects.

(6) As one aspect of the present embodiment, for each period of acquiring each of a plurality of frame images, the control system may cause at least any A/D converter to execute a dummy A/D conversion. Thus, the A/D converter executes the dummy A/D conversion each time the solid-state imaging device acquires a frame image, enabling more effective reduction of linear noise appearing in an integrated image.

(7) As one aspect of the present embodiment, it is preferable that the control system and the L pieces of A/D converter are connected by L pieces of wiring that are electrically independent from each other. In particular, it is preferable that lengths of these L pieces of wiring are equal to each other. Note that the L pieces of wiring arranged between the control system and the L pieces of A/D converter are wirings to output a control signal (A/D conversion control signal) for controlling an A/D conversion timing from the control system to the selected A/D converter among the L pieces of A/D converter. This allows effective suppression of deviation in an arrival timing of the control signal between the plurality of A/D converters.

(8) Further, as one aspect of the present embodiment, a time interval of A/D conversions (conversion from analog signals to digital signals) executed for each column of an (m+1)-th row is preferably equal to a time interval from a last dummy A/D conversion among dummy A/D conversions executed during a period from an A/D conversion of a last column of an m-th row to the A/D conversion of the first column of the (m+1)-th row to an A/D conversion of a first column of the (m+1)-th row. This allows a dummy A/D conversion executed once or more times to simulate the A/D conversion of each column, enabling effective suppression of a change in the output characteristic of the A/D converter.

(9) As one aspect of the present embodiment, in addition to A/D conversion control in each of the L pieces of A/D converter, the control system may give an instruction on each operation timing of row selection by the row selection unit and column selection by the column selection unit. In this case, the control system may have a structure to perform operation control of an A/D conversion and operation control of the row selection and the column selection independently from each other. For example, in accordance with a common operation clock supplied from outside, a first control unit performs operation control of the A/D conversion, while a second control unit performs operation control of the row selection and the column selection. Meanwhile, naturally, the operation control of the A/D conversion, the operation control of the row selection, and the operation control of the column selection may be performed by a single control unit in accordance with an operation clock supplied from outside.

As described above, each aspect listed in this Description of Embodiment of Present Invention can be applied to all of the remaining aspects or to all combinations of these remaining aspects.

Details of Embodiment of Present Invention

Hereinafter, a specific structure of the solid-state imaging device, the radiation imaging system, and the method of controlling the solid-state imaging device according to the present embodiment will be described in detail with reference to the attached drawings. It should be noted that the present invention is not limited to these illustrative examples, but is indicated by the claims, and it is intended to include meanings equivalent to the claims and all modifications within the scope. Moreover, in the description of the drawings, the same elements are denoted by the same reference numerals, and redundant descriptions are omitted.

First Embodiment

FIG. 1 is a diagram showing a configuration of a medical X-ray imaging system 100 (configuration common to first and second embodiments) as an example of a radiation imaging system according to the present embodiment. Particularly, in the X-ray imaging system 100 according to the first embodiment, a passive pixel sensor (PPS) solid-state imaging device to be described later is applied as an example of the solid-state imaging device according to the present embodiment. In addition, the X-ray imaging system 100 has imaging modes such as panoramic imaging (panoramic radiography), cephalometric imaging (cephalometric radiography), and CT imaging (CT shooting) mainly in dentistry, and captures an X-ray image of a jaw of an examinee. The X-ray imaging system 100 comprises a solid-state imaging device and an X-ray generator, and captures an image (X-ray image) formed by X-rays that are outputted from the X-ray generator and are transmitted through a subject A (that is, the jaw of the examinee), by the solid-state imaging device.

The X-ray imaging system 100 shown in FIG. 1 comprises a solid-state imaging device 1A, an X-ray source 106 (radiation source), a moving mechanism (swing arm 104) to move the solid-state imaging device 1A and the X-ray source 106 relative to the subject A, and an image generation unit 200.

The X-ray source 106 is a radiation source to generate X-rays that are emitted toward the subject A. An irradiation field of X-rays generated from the X-ray source 106 is controlled by a primary slit plate 106b. The X-ray source 106 contains an X-ray tube. Adjustment of conditions such as a tube voltage, a tube current, and an energization time of the X-ray tube allows control of an amount of X-ray irradiation to the subject A. Further, the X-ray source 106 outputs X-rays at a predetermined divergence angle in a certain imaging mode by controlling an opening range of the primary slit plate 106b. Whereas, in another imaging mode, the X-ray source 106 can output X-rays at a divergence angle narrower than this predetermined divergence angle.

The solid-state imaging device 1A is a CMOS solid-state imaging device having a plurality of pixels arranged two-dimensionally, and converts an X-ray image having passed through the subject A into electrical image data D. In front of the solid-state imaging device 1A, a secondary slit plate 107 to limit an X-ray incidence region is provided. A rotation control system 108 rotatably supports the solid-state imaging device 1A around an axis C perpendicular to a surface of a light receiving part 2 of the solid-state imaging device 1A, and rotates the solid-state imaging device 1A at a predetermined angular position according to imaging modes such as CT imaging, panoramic imaging, and cephalometric imaging.

The swing arm 104 turns the X-ray source 106 and the solid-state imaging device 1A around the subject A in a state of holding the X-ray source 106 and the solid-state imaging device 1A facing each other, during CT imaging or panoramic imaging. Further, at a time of cephalometric imaging, there is provided a slide mechanism 113 to linearly displace the solid-state imaging device 1A with respect to the subject A. The swing arm 104 is driven by an arm motor 109 constituting a rotary table, and a rotation angle of the swing arm is detected by an angle sensor 112. Further, the arm motor 109 is mounted on a movable portion of an XY table 114, and a center of rotation is optionally adjusted in a horizontal plane.

The image data D outputted from the solid-state imaging device 1A is temporarily taken in by a central processing unit (CPU) 121 constituting a part of the image generation unit 200, and then stored in a frame memory 122. From the image data stored in the frame memory 122, a tomographic image along any tomographic plane and a panoramic image are reproduced by predetermined arithmetic processing. The reproduced tomographic image and the panoramic image are outputted to a video memory 124, then displayed on an image display unit (display) 125, and used in various diagnoses. Note that the image generation unit 200 of the radiation i imaging system according to the present embodiment comprises at least the CPU 121 and the frame memory 122 shown in FIG. 1.

The CPU 121 is connected with a work memory 123 required for signal processing, and also connected with an operation panel 119 having a panel switch, an X-ray irradiation switch, and the like. Further, the CPU 121 is connected to each of a motor drive circuit 111 configured to drive the arm motor 109, slit control circuits 115 and 116 configured to control opening ranges of the primary slit plate 106b and the secondary slit plate 107, and an X-ray control circuit 118 configured to control the X-ray source 106. Further, the CPU 121 outputs a clock signal for driving the solid-state imaging device 1A. The X-ray control circuit 118 performs feedback control on an X-ray irradiation dose to the subject based on a signal captured by the solid-state imaging device 1A.

Figure 2:
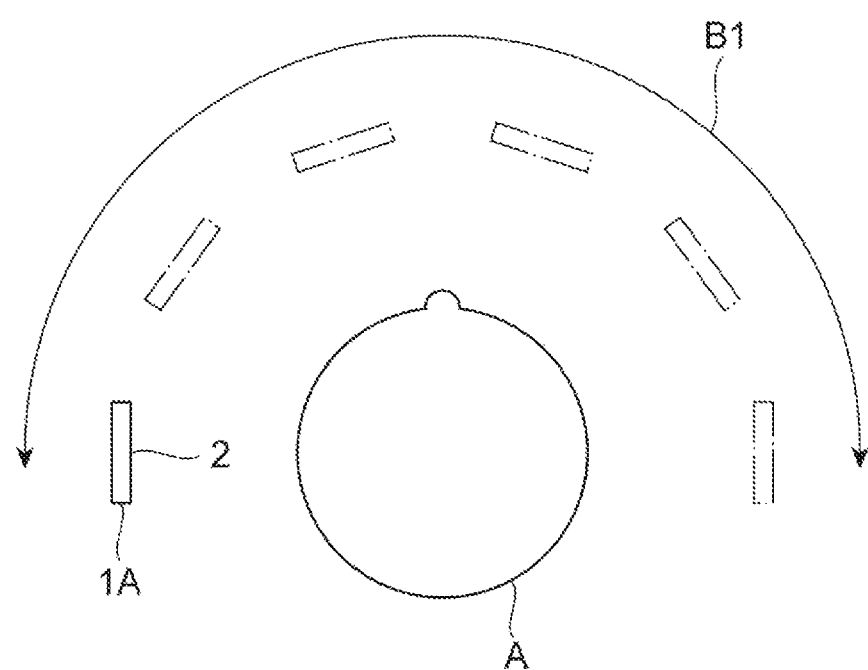
FIG. 2 is a view showing a state where a solid-state imaging device according to the present embodiment turns and moves around a subject as seen from above the subject.

FIG. 2 is a view showing a state where the solid-state imaging device 1A turns and moves around the subject A as seen from above the subject A (the jaw of the examinee). Note that, in FIG. 2, a trajectory of the solid-state imaging device 1A is indicated by a one dotted chain line. While moving on a horizontal plane along a circumferential direction (a direction B1 shown in FIG. 2) around the subject A by the swing arm 104, the solid-state imaging device 1A captures an X-ray image of the subject A (an image represented by X-rays having passed through the subject A). At this time, an orientation of the solid-state imaging device 1A is set such that the light receiving part 2 of the solid-state imaging device 1A always faces the subject A.

Figure 3:
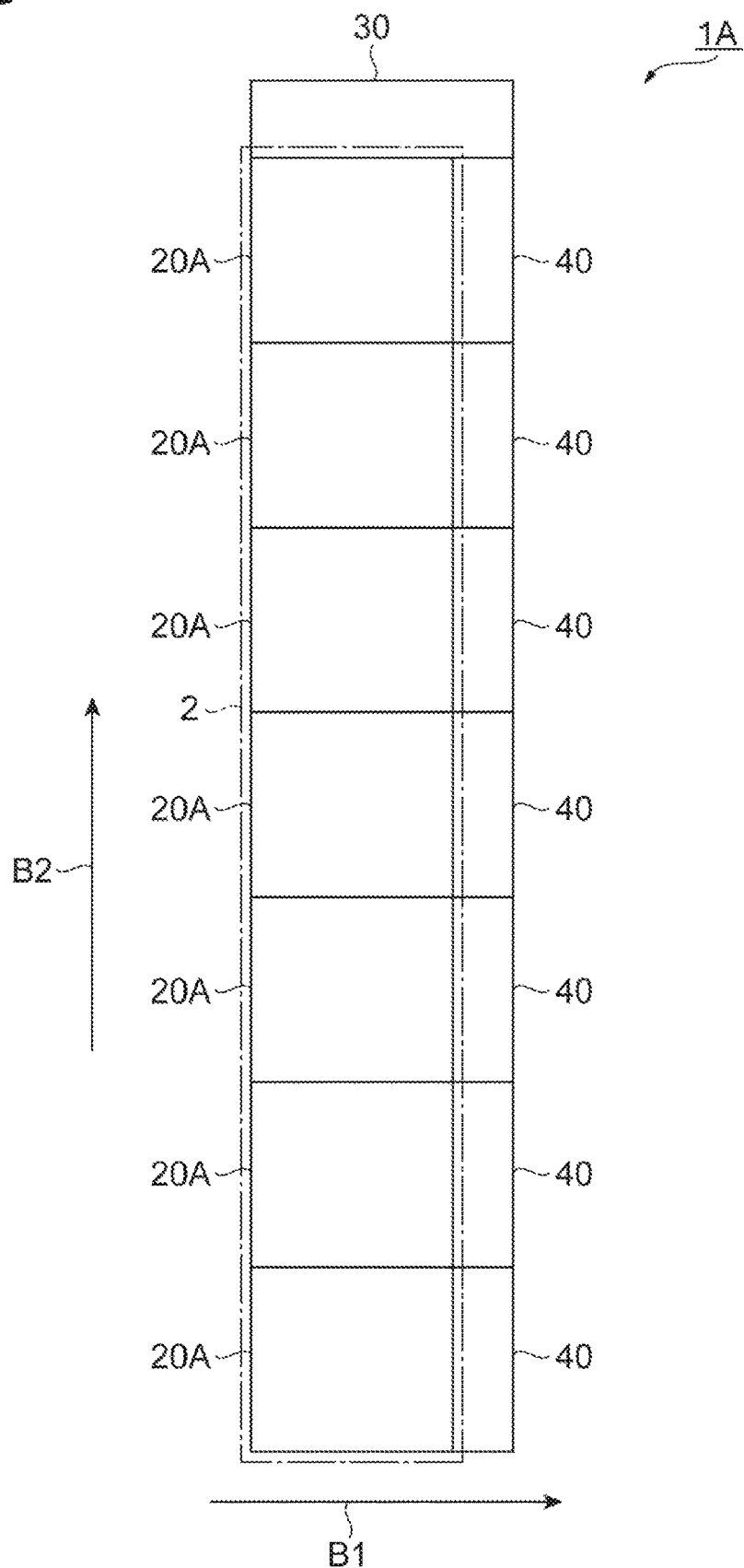
FIG. 3 is a plan view showing a schematic configuration of the solid-state imaging device according to the present embodiment.

FIG. 3 is a plan view showing a schematic configuration of the solid-state imaging device 1A. As shown in FIG. 3, the solid-state imaging device 1A has the elongated light receiving part 2 extending along a certain direction B2. The light receiving part 2 has L (an integer of 2 or more) pieces of imaging pixel region 20A. Each of the L pieces of imaging pixel region 20A is arranged in a line along the direction B2, and adjacent imaging pixel regions 20A are in contact with each other. An arrow B1 in FIG. 3 represents a moving direction of the solid-state imaging device 1A during panoramic imaging. That is, during panoramic imaging, a longitudinal direction B2 of the light receiving part 2 (arrangement direction of the imaging pixel regions 20A) and a moving direction B1 cross each other (orthogonal in the example of FIG. 3). Note that the moving direction B1 is a predetermined direction to be a reference in the present embodiment.

The solid-state imaging device 1A further comprises a vertical shift register unit 30 (row selection unit) and L pieces of signal output unit 40. The vertical shift register unit 30 is arranged along one (or both) of a pair of side edges, which crosses the longitudinal direction B2, of the light receiving part 2. The L pieces of signal output unit 40 are arranged side by side along an end side of the light receiving part 2 extending along the longitudinal direction B2, and respectively correspond to the L pieces of imaging pixel region 20A. In the example of FIG. 3, each signal output unit 40 is arranged adjacent to the corresponding imaging pixel region 20A. Meanwhile, the vertical shift register unit 30 may be provided on a single substrate to be aligned with the light receiving part 2, or may be provided on a separate substrate from the light receiving part 2. Similarly, the L pieces of signal output unit 40 may be provided on single substrate to be aligned with the light receiving part 2, or may be provided on a separate substrate from the light receiving part 2.

In addition, the solid-state imaging device 1A further comprises a scintillator (not shown) provided on the light receiving part 2. The scintillator generates scintillation light in response to incident X-rays to convert an X-ray image into a light image, and outputs this light image to the light receiving part 2. The scintillator is installed so as to cover the light receiving part 2, or is provided on the light receiving part 2 by vapor deposition.

Figure 4:
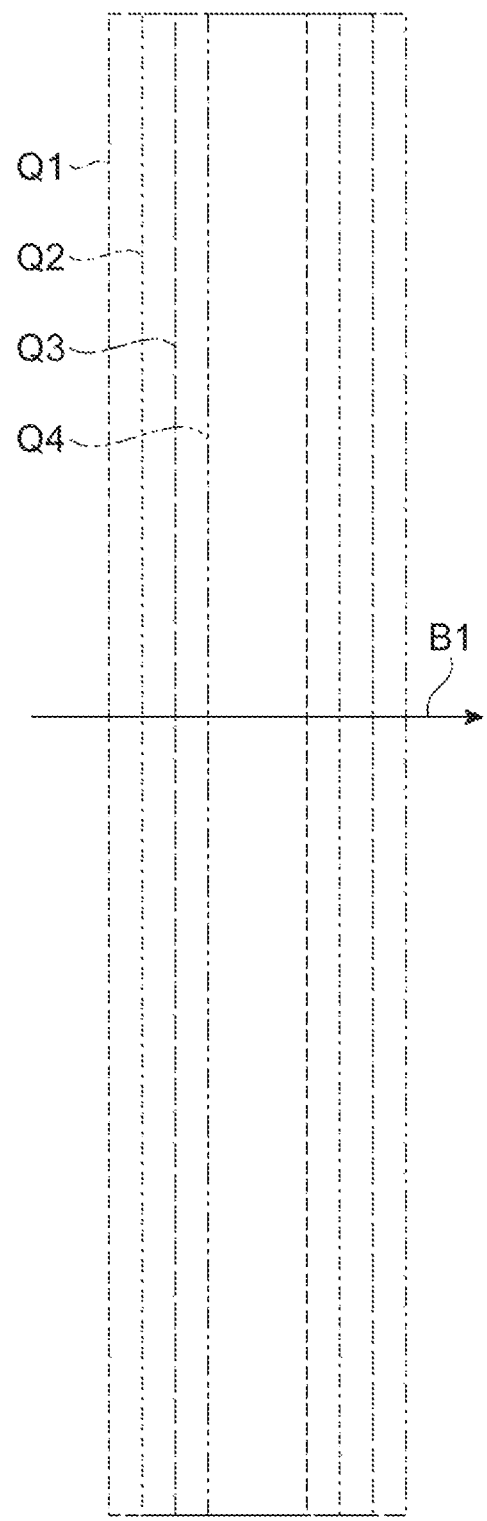
FIG. 4 is a view for explaining a method of creating image data in panoramic imaging.

FIG. 4 is a view for explaining a method of creating image data in panoramic imaging. A plurality of squares having different line types indicate frame images Q1 to Q4 each at different timings. As shown in FIG. 4, during panoramic imaging, the solid-state imaging device 1A repeatedly performs imaging while moving along the direction B1, and acquires the plurality of frame images Q1 to Q4 in which a position in the direction B1 is gradually shifted. A shift amount of each frame image is determined by a product of a moving speed of the solid-state imaging device 1A and an imaging cycle. The plurality of frame images Q1 to Q4 acquired by the solid-state imaging device 1A are integrated in a computer (e.g., the CPU 121). Meanwhile, in the computer during the integration, each of these frame images Q1 to Q4 can be shifted along an axial direction corresponding to a moving direction by a movement amount corresponding to the moving speed. This enables generation of a panoramic image extending along the direction B1.

Figure 5:
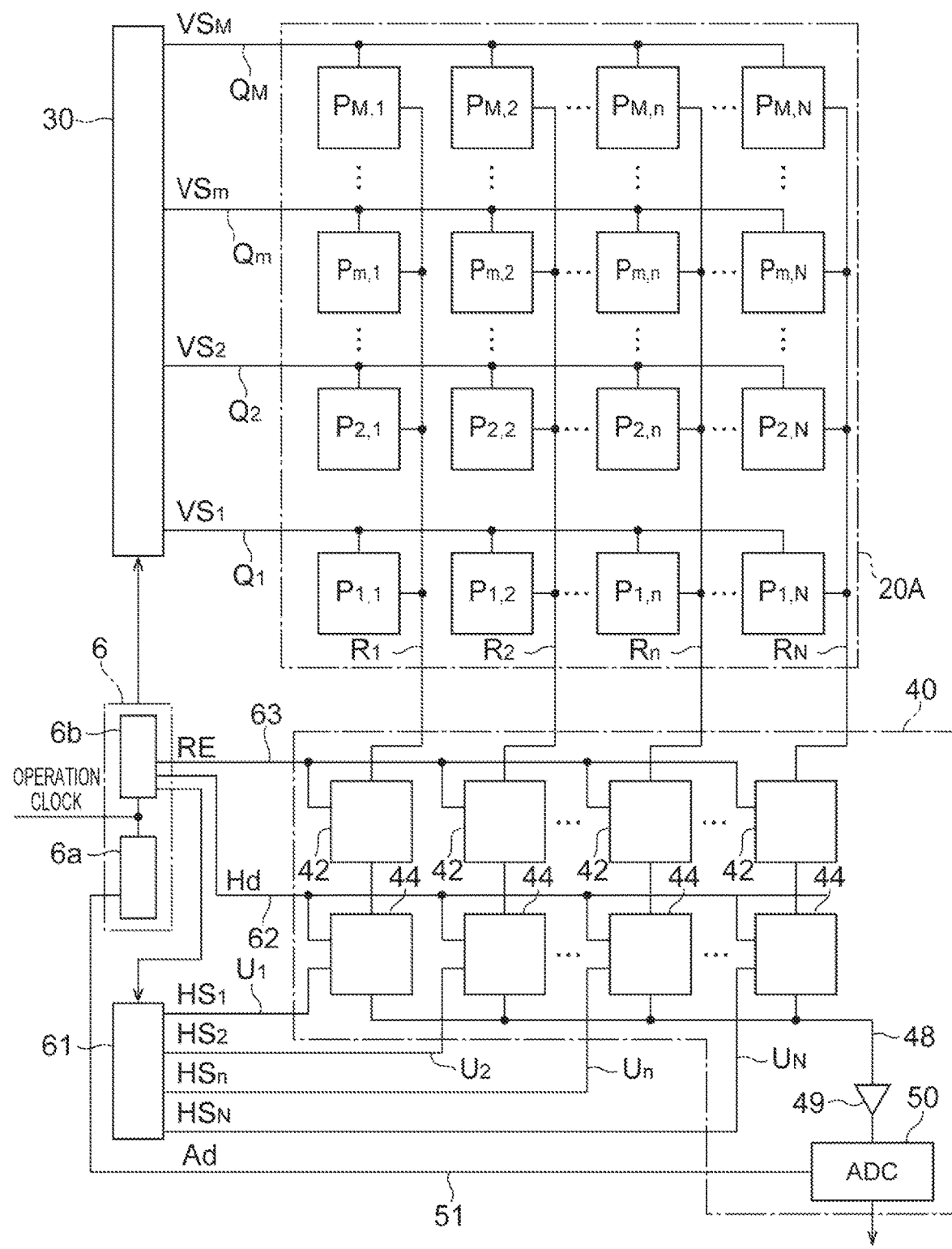
FIG. 5 is a diagram showing a configuration of an imaging pixel region and a signal output unit in a PPS solid-state imaging device (an example of the solid-state imaging device according to the present embodiment) applied to the radiation imaging system of FIG. 1.

Here, a detailed configuration of each imaging pixel region 20A and each signal output unit 40 of the solid-state imaging device 1A will be described. FIG. 5 is a diagram showing a configuration of the imaging pixel region 20A and the signal output unit 40 in a PPS solid-state imaging device as the solid-state imaging device 1A (an example of the solid-state imaging device according to the present embodiment). Note that, in order to simplify the description, FIG. 5 shows a configuration example of a PPS solid-state imaging device including one imaging pixel region 20A and one signal output unit 40. This PPS solid-state imaging device constitutes a part of the radiation imaging system according to the first embodiment. The imaging pixel region 20A forms an M-row by N-column matrix by two-dimensionally arranging M (an integer of 2 or more)×N (an integer of 2 or more) pieces of pixel $P_{1,1}$ to $P_{M,N}$. Each row of the M-row by N-column matrix extends along the longitudinal direction B2 of the light receiving part 2 shown in FIG. 3. Each column extends along a direction orthogonal to the longitudinal direction B2 of the solid-state imaging device 1A shown in FIG. 3 (that is, along the moving direction B1). N pieces of pixel $P_{m,1}$ to $P_{m,N}$ of an m-th row (m=1, 2, . . . , M) are connected to the vertical shift register unit 30 via an m-th row selection wiring $Q_m$. The vertical shift register unit 30 is electrically connected to the control system 6 and controlled by the control system 6. Further, M pieces of pixel $P_{1,n}$ to $P_{M,n}$ of an n-th column (n=1, 2, . . . , N) are connected to the signal output unit 40 via an n-th column readout wiring $R_n$. Note that the control system 6 can be constituted by a single control unit, but in the example of FIG. 5, the control system 6 is constituted by a plurality of control units configured to operate in accordance with an operation clock supplied from outside, specifically, constituted by a first control unit 6a and a second control unit 6b. Therefore, in the example of FIG. 5, the vertical shift register unit 30 is electrically connected to the first control unit 6a and is controlled by the first control unit 6a.

The signal output unit 40 has N pieces of integration circuit 42 and N pieces of hold circuit 44 provided for each column. The integration circuit 42 and the hold circuit 44 are connected to each other in series for each column. The N pieces of integration circuit 42 have a configuration common to each other. Further, the N pieces of hold circuit 44 have a configuration common to each other.

The N pieces of integration circuit 42 respectively have input ends connected to respective readout wirings $R_1$ to $R_N$, accumulate charges inputted from the readout wirings $R_1$ to $R_N$ to the input ends, and output a voltage value (analog signal) corresponding to an accumulated charge quantity from output ends to the respective N pieces of hold circuit 44. Each of the N pieces of integration circuit 42 is connected to the first control unit 6a via a reset wiring 63 commonly provided for the N pieces of integration circuit 42. Each of the N pieces of hold circuit 44 has an input end connected to the output end of the integration circuit 42, holds a voltage value inputted to this input end, and outputs the held voltage value from an output end to an output wiring 48. Each of the N pieces of hold circuit 44 is connected to the first control unit 6a via a hold wiring 62 provided in common for the N pieces of hold circuit 44. Further, each of the N pieces of hold circuit 44 is connected to a horizontal shift register unit 61 (column selection unit) via each of a first column selection wiring $U_1$ to an N-th column selection wiring $U_N$. The horizontal shift register unit 61 is electrically connected to the first control unit 6a and is controlled by the first control unit 6a. Meanwhile, one common control system 6 may be provided for the L pieces of signal output unit 40, or L pieces of control system 6 may be provided corresponding to the respective L pieces of signal output unit 40.

The signal output unit 40 further comprises an amplifier 49 and an A/D converter 50. The output wiring 48 is connected to the A/D converter 50 via the amplifier 49. The A/D converter 50 converts a voltage value transmitted via the output wiring 48 into a digital signal to become a frame image. In the present embodiment, the L pieces of A/D converter 50 are respectively provided corresponding to the L pieces of imaging pixel region 20A. The A/D converter 50 is connected to the second control unit 6b via an A/D conversion control wiring 51. The second control unit 6b supplies an A/D conversion control signal Ad to the A/D converter 50 via the A/D conversion control wiring 51. The number of the provided A/D conversion control wirings 51 is L, to correspond to the L pieces of A/D converter 50. Lengths of the L pieces of A/D conversion control wiring 51 are equal to each other.

The A/D conversion control signal Ad controls a conversion timing of the A/D converter 50. For example, with a rise of the A/D conversion control signal Ad from a non-significant value (e.g., low level) to a significant value (e.g., high level) as a trigger, the A/D converter 50 starts a conversion operation.

Under the control of the first control unit 6a, the vertical shift register unit 30 supplies an m-th row selection control signal $VS_m$, to each of the N pieces of pixel $P_{m, 1}$ to $P_{m, N}$ of the m-th row via the m-th row selection wiring $Q_m$. In the vertical shift register unit 30, row selection control signals $VS_1$ to $VS_M$ are sequentially set to significant values, and charges generated in the plurality of pixels $P_{1, 1}$ to $P_{M, N}$ are outputted for each row. Further, under the control of the first control unit 6a, the horizontal shift register unit 61 supplies column selection control signals $HS_1$ to $HS_N$ to each of the N pieces of hold circuit 44 via the column selection wirings $U_1$ to $U_N$. In the horizontal shift register unit 61, the column selection control signals $HS_1$ to $HS_N$ are sequentially set to significant values, and voltage values held in the hold circuit 44 are outputted to the output wiring 48 for each column. In addition, the first control unit 6a supplies a reset control signal RE to each of the N pieces of integration circuit 42 via the reset wiring 63, and supplies a hold control signal Hd to each of the N pieces of hold circuit 44 via the hold wiring 62.

Figure 6:
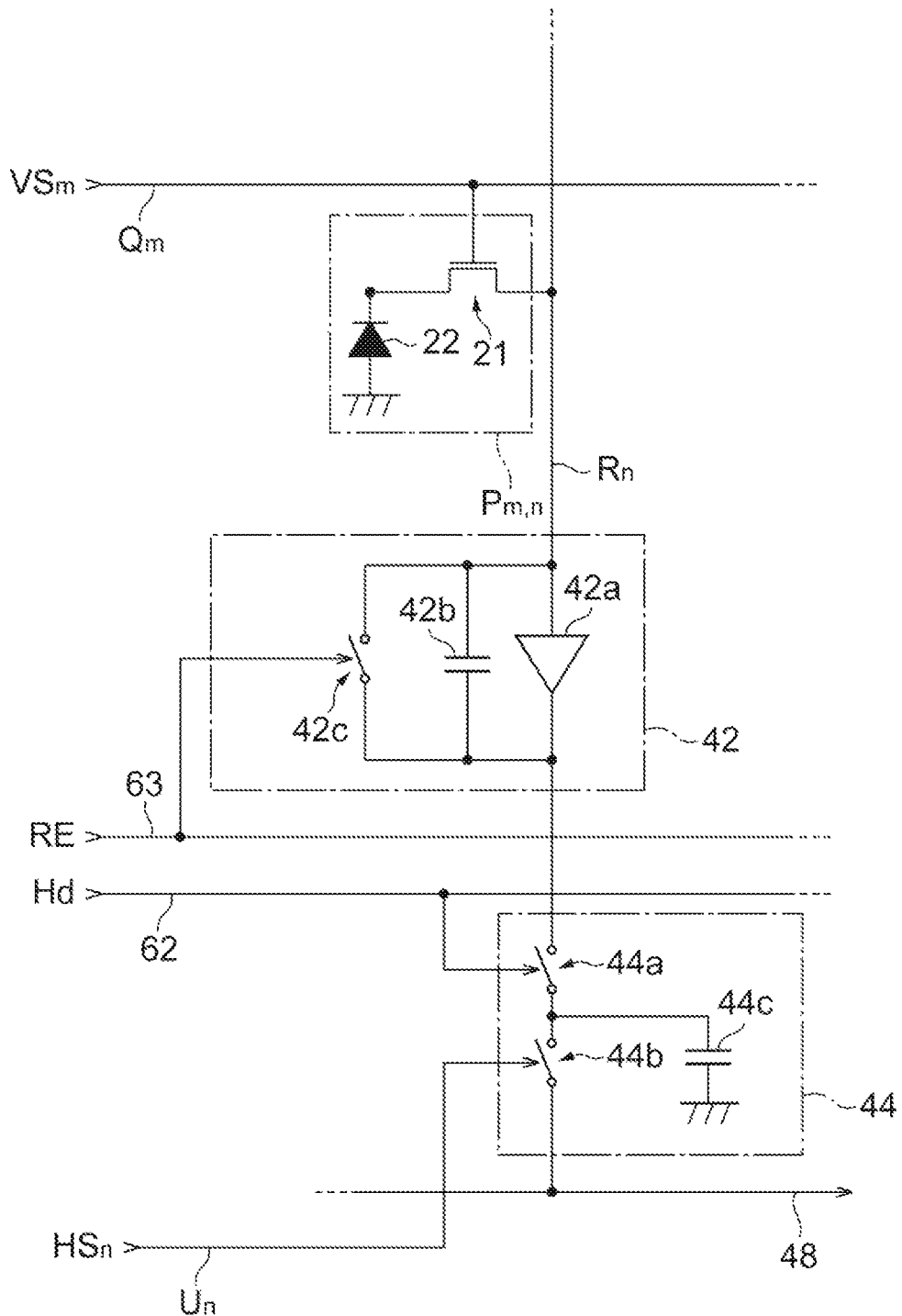
FIG. 6 is a diagram showing an example of a circuit configuration of each of a pixel, an integration circuit, and a hold circuit of the solid-state imaging device according to the present embodiment.

FIG. 6 is a diagram showing an example of a circuit configuration of each of a pixel $P_{m, n}$, the integration circuit 42, and the hold circuit 44 of the solid-state imaging device 1A. Note that FIG. 6 shows a circuit diagram of the pixel $P_{m, n}$ as a representative for the M×N pieces of pixel $P_{1, 1}$ to $P_{M, N}$.

As shown in FIG. 6, the pixel $P_{m, n}$ is provided with a transistor 21 as a readout switch, and a photodiode 22. One current terminal of the transistor 21 is connected to a cathode terminal of the photodiode 22. An anode terminal of the photodiode 22 is grounded. Further, the other current terminal of the transistor 21 is connected to a corresponding readout wiring (e.g., the n-th column readout wiring $R_n$ in a case of the pixel $P_{m, n}$). A control terminal of the transistor 21 is connected to a corresponding row selection wiring (e.g., the m-th row selection wiring $Q_m$ in a case of the pixel $P_{m, n}$). To the transistor 21, the m-th row selection control signal $VS_m$ is supplied via the m-th row selection wiring $Q_m$. The m-th row selection control signal $VS_m$ gives an instruction on opening and closing operations of the transistor 21 included in each of the N pieces of pixel $P_{m, 1}$ to $P_{m, N}$ of the m-th row. For example, when the m-th row selection control signal $VS_m$, has a non-significant value (e.g., low level), the transistor 21 enters a non-conductive state. At this time, charges generated in the photodiode 22 are accumulated in a junction capacitance section of the photodiode 22 without being outputted to the readout wiring $R_n$. Whereas, when the m-th row selection control signal $VS_m$ has a significant value (e.g., high level), the transistor 21 enters a connected state. At this time, the charges accumulated in the junction capacitance section of the photodiode 22 (that is, an electric signal having a magnitude corresponding to an amount of incident light) is outputted to the readout wiring $R_n$ via the transistor 21. These charges are transmitted to the integration circuit 42 via the readout wiring $R_n$.

The integration circuit 42 includes an amplifier 42a, a capacitive element 42b, and a discharge switch 42c. The capacitive element 42b and the discharge switch 42c are connected in parallel to each other and are connected between an input terminal and an output terminal of the amplifier 42a. The input terminal of the amplifier 42a is connected to the readout wiring $R_n$. To the discharge switch 42c, the reset control signal RE is supplied via the reset wiring 63.

The reset control signal RE gives an instruction on opening and closing operations of the discharge switch 42c of each of the N pieces of integration circuit 42. For example, when the reset control signal RE has a significant value (e.g., high level), the discharge switch 42c is closed, the capacitive element 42b is discharged, and an output voltage value of the integration circuit 42 is initialized. Further, when the reset control signal RE has a non-significant value (e.g., low level), the discharge switch 42c is opened, charges inputted to the integration circuit 42 are accumulated in the capacitive element 42b, and a voltage value corresponding to an accumulated charge quantity is outputted from the integration circuit 42 to the output wiring 48 via the hold circuit 44.

The hold circuit 44 holds a voltage value before being outputted to the output wiring 48 for each column. The hold circuit 44 includes an input switch 44a, an output switch 44b, and a capacitive element 44c. One end of the capacitive element 44c is grounded. The other end of the capacitive element 44c is connected to the output end of the integration circuit 42 via the input switch 44a, and is connected to the output wiring 48 via the output switch 44b. To the input switch 44a, the hold control signal Hd is supplied via the hold wiring 62. The hold control signal Hd gives an instruction on opening and closing operations of the input switch 44a of each of the N pieces of hold circuit 44. To the output switch 44b of the hold circuit 44, an n-th column selection control signal $HS_n$ is supplied via an n-th column selection wiring $U_n$. The selection control signal $HS_n$ gives an instruction on opening and closing operations of the output switch 44b of the hold circuit 44.

For example, when the hold control signal Hd changes from low level to high level, the input switch 44a changes from a closed state to an open state. At that time, a voltage value inputted to the hold circuit 44 is held in the capacitive element 44c. Further, when the n-th column selection control signal $HS_{11}$ changes from low level to high level, the output switch 44b is closed, and the voltage value held in the capacitive element 44c is outputted to the output wiring 48.

Figure 7:
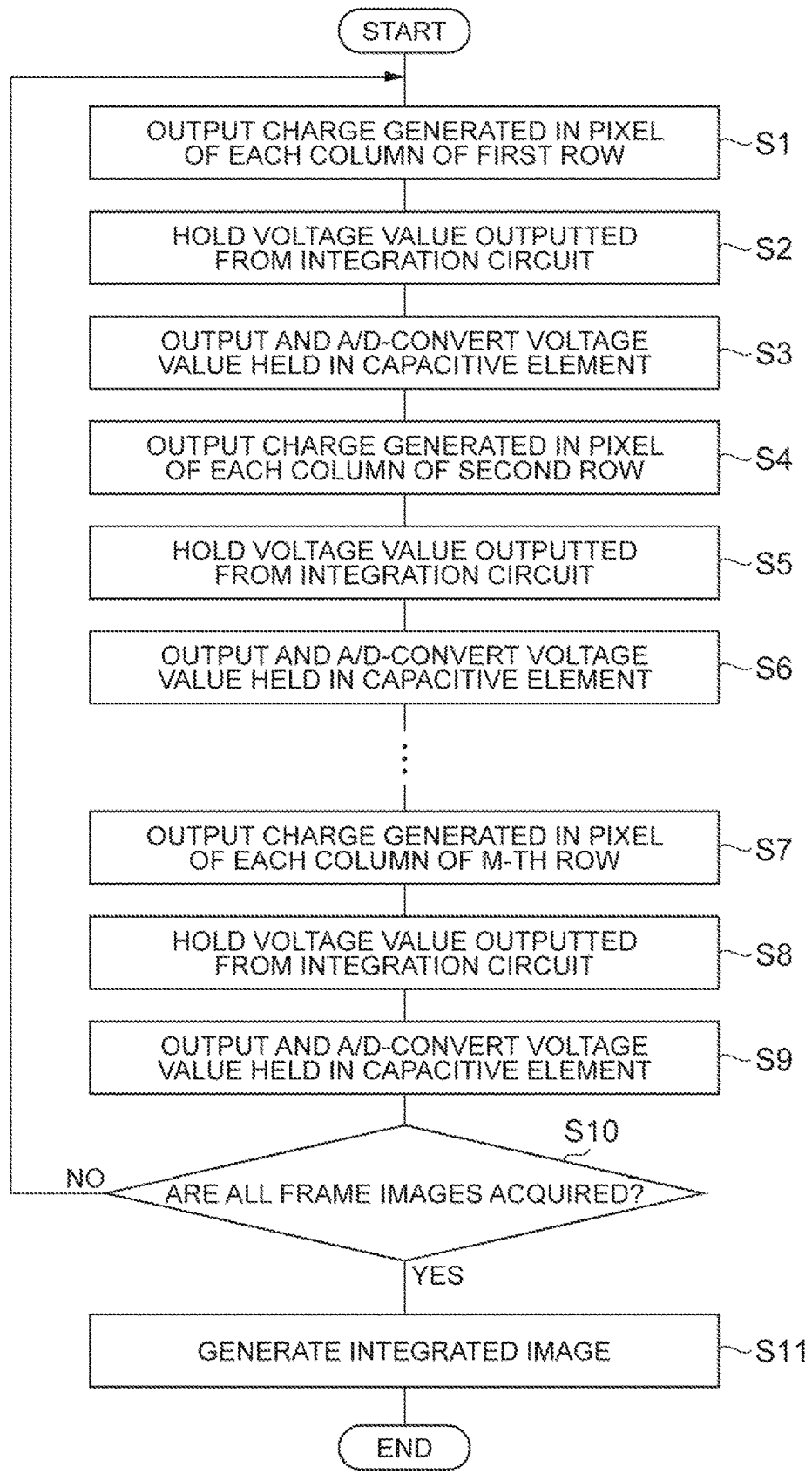
FIG. 7 is a flowchart showing a method of controlling the solid-state imaging device according to the present embodiment.
Figure 8:
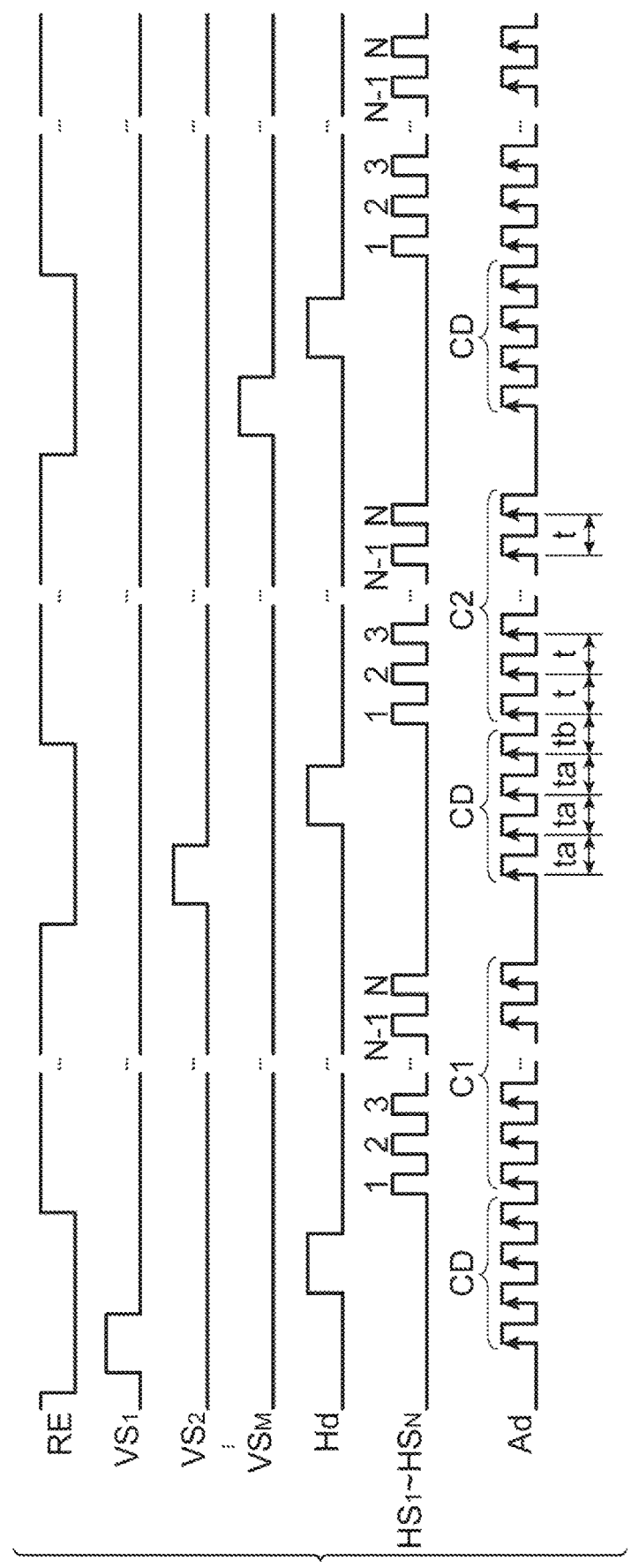
FIG. 8 is a timing chart of individual signals inputted to the imaging pixel region and the signal output unit.

Here, an operation of the solid-state imaging device 1A will be described together with the method of controlling the solid-state imaging device 1A. FIG. 7 is a flowchart showing the method of controlling the solid-state imaging device 1A according to the present embodiment. FIG. 8 is a timing chart of individual signals inputted to the imaging pixel region 20A and the signal output unit 40. FIG. 8 shows, in order from the top, each of the reset control signal RE, a first row selection control signal $VS_1$, a second row selection control signal $VS_2$, an M-th row selection control signal $VS_M$, the hold control signal Hd, a first column selection control signal $HS_1$ to an N-th column selection control signal $HS_N$, and the A/D conversion control signal Ad.

First, the first control unit 6a sets the reset control signal RE to high level. This causes the discharge switch 42c to be in a closed state in each of the N pieces of integration circuit 42, and the capacitive element 42b is discharged. Thereafter, the first control unit 6a sets the reset control signal RE to low level.

Next, charges generated in pixels of respective columns of the first row are outputted (step S1). Specifically, the vertical shift register unit 30 sets the first row selection control signal $VS_1$ to a significant value (high level). This causes the transistor 21 to be in a connected state in the pixels $P_{1,1}$ to $P_{1,N}$ of the first row, and charges accumulated in the photodiodes 22 of the respective pixels $P_{1,1}$ to $P_{1,N}$ are outputted to the integration circuit 42 through the readout wirings $R_1$ to $R_N$, and accumulated in the capacitive element 42b. From the integration circuit 42, a voltage value having a magnitude corresponding to a charge quantity accumulated in the capacitive element 42b is outputted. Thereafter, the transistors 21 of the respective pixels $P_{1,1}$ to $P_{1,N}$ of the first row enter a disconnected state. Then, the first control unit 6a sets the hold control signal Hd to high level. This causes the input switch 44a to be in a connected state in each of the N pieces of hold circuit 44, and a voltage value outputted from the integration circuit 42 is held by the capacitive element 44e (step S2).

Subsequently, the voltage value (analog signal) held in the capacitive element 44c is outputted to the output wiring 48 for each column (step S3). Specifically, the horizontal shift register unit 61 sequentially sets the first column selection control signal $HS_1$ to the N-th column selection control signal $HS_N$ to high level. This causes the output switches 44b of the N pieces of hold circuit 44 to be in a closed state sequentially, and the voltage values (analog signals) held in the capacitive element 44c are sequentially outputted to the output wiring 48. Further, during this time, the first control unit 6a sets the reset control signal RE to high level, and the capacitive element 42b of the integration circuit 42 is discharged.

Meanwhile, in step S3, in parallel with the above operation, the voltage value (analog signal) outputted to the output wiring 48 is converted into a digital signal by the A/D converter 50 (first A/D conversion step). Specifically, every time the horizontal shift register unit 61 sets each column selection control signal $HS_n$ to high level, the second control unit 6b raises the A/D conversion control signal Ad from low level to high level. This raising operation is performed while each column selection control signal $HS_n$ is at high level. This causes each voltage value of each column, which is an analog signal outputted to the output wiring 48, to be converted into a digital signal. These digital signals are outputted to the CPU 121 (see FIG. 1) as pixel data of a first row of one frame image.

Subsequently, charges generated in pixels of respective columns of a second row are outputted (step S4). Specifically, the vertical shift register unit 30 sets the second row selection control signal $VS_2$ to high level. This causes the transistor 21 to be in a connected state in pixels $P_{2,1}$ to $P_{2,N}$ of the second row, and charges accumulated in the photodiodes 22 of the respective pixels $P_{2,1}$ to $P_{2,N}$ are outputted to the integration circuit 42 through the readout wirings $R_1$ to $R_N$, and accumulated in the capacitive element 42b. From the integration circuit 42, a voltage value having a magnitude corresponding to a charge quantity accumulated in the capacitive element 42b is outputted. Thereafter, the transistors 21 of the respective pixels $P_{2,1}$ to $P_{2,N}$ of the second row enter a disconnected state.

When the voltage value outputted from the integration circuit 42 is held by the capacitive element 44c (step S5), the voltage value held in the capacitive element 44c is subsequently outputted to the output wiring for each column (step S6). At this time, in step S6, in parallel with the above operation, the voltage value outputted to the output wiring 48 is converted into a digital signal in the A/D converter 50 (second A/D conversion step). Meanwhile, details of these steps S5 and S6 are similar to the above-described steps S2 and S3, respectively.

Thereafter, for a third row to an M-th row as well, an operation similar to that for the first row and the second row causes a voltage value having a magnitude corresponding to a charge quantity accumulated in the capacitive element 42b to be sequentially outputted from the N pieces of hold circuit 44 to the output wiring 48, and converted into a digital signal (steps S7 to S9). In this way, reading of one frame image from the L pieces of imaging pixel region 20A is completed. The solid-state imaging device 1A acquires a plurality of frame images by repeatedly performing such an operation during movement of the solid-state imaging device 1A (step S10). For example, the CPU 121 integrates the acquired plurality of frame images while shifting the frame images along an axis corresponding to a moving direction of the solid-state imaging device 1A by a distance corresponding to a moving speed of the solid-state imaging device 1A. This causes one panoramic image to be created (step S11).

Here, in the present embodiment, one or a plurality of times of dummy A/D conversion are executed, after the A/D converter 50 converts a voltage value of the m-th row into a digital signal before converting a voltage value of the (m+1)-th row into a digital signal. The dummy A/D conversion is an A/D conversion executed in a state where the A/D converter does not receive a significant voltage value. For example, after providing the A/D conversion control signal Ad with a rise (symbol C1 in FIG. 8) corresponding to the first to M-th columns of the first row, before providing the A/D conversion control signal Ad with a rise (symbol C2 in FIG. 8) corresponding to the first to M-th columns of the second row, the second control unit 6b provides the A/D conversion control signal Ad with a rise (symbol CD in FIG. 8) of a dummy A/D conversion. This rise of a dummy A/D conversion may be once or a plurality of times (FIG. 8 illustrates a case of four times). The second control unit 6b also performs similar processing for third and subsequent rows. That is, after providing the A/D conversion control signal Ad with a rise corresponding to the first to M-th columns of the m-th row, before providing the A/D conversion control signal Ad with a rise corresponding to the first to M-th columns of the (m+1)-th row, the second control unit 6b provides the A/D conversion control signal Ad with a rise CD of a dummy A/D conversion.

The dummy A/D conversion of the A/D converter 50 is a conversion operation simulating the A/D conversion for the first to M-th columns. Therefore, at least one (preferably both) of a time interval to between a plurality of times of dummy A/D conversion, and a time interval tb between the A/D conversion of the first row and the last dummy A/D conversion among one or a plurality of times of dummy A/D conversion is preferably equal to a time interval t of the A/D conversion between the respective columns of the first row to the N-th row.

Further, in a period during which a rise of a dummy A/D conversion is given to the (m+1)-th row, charges are outputted from respective pixels $P_{m+1,\ 1}$ to $P_{m+1,\ N}$ of the (m+1)-th row when the (m+1)-th row selection control signal $VS_{m+1}$ becomes high level, and the charges are converted into a voltage value by the integration circuit 42. Thereafter, the hold control signal Hd becomes high level, and the voltage values corresponding to the charges from the respective pixels $P_{m+1,\ 1}$ to $P_{m+1,\ N}$ of the (m+1)-th row are respectively held in the hold circuits 44. That is, in the present embodiment, in parallel with the reading of charges from the pixels $P_{m+1,\ 1}$ to $P_{m+1,\ N}$ of the (m+1)-th row and the holding of the voltage value corresponding to the charges, a dummy A/D conversion of the A/D converter 50 is performed.

Meanwhile, in the present embodiment, the dummy A/D conversion is executed not only between the A/D conversion in the m-th row and the A/D conversion in the (m+1)-th row, but also executed immediately before the A/D conversion in the first row. That is, as shown in FIG. 8, even before providing the A/D conversion control signal Ad with a rise (symbol C1 in FIG. 8) corresponding to the first to M-th columns of the first row, the second control unit 6b provides the A/D conversion control signal Ad with a rise (symbol CD in FIG. 8) of a dummy A/D conversion.

Such a dummy A/D conversion of the A/D converter 50 may be performed in all of a plurality of times of imaging processing for respectively obtaining a plurality of frame images, or may be performed in at least one optional imaging processing, as required. Further, in the above example, the dummy A/D conversion of the A/D converter 50 is performed during reading processing of all the first row to the M-th row, but may be performed during reading processing of at least one optional row, as required. Further, in acquiring one frame image, a dummy A/D conversion may be executed in all of the L pieces of A/D converter 50 respectively corresponding to the L pieces of imaging pixel region 20A, or the dummy A/D conversion may be executed in some A/D converters (L1 pieces of A/D converter) 50 among the L pieces of A/D converter 50. Note that L1 is an integer of 2 or more and less than L.

Figure 9:
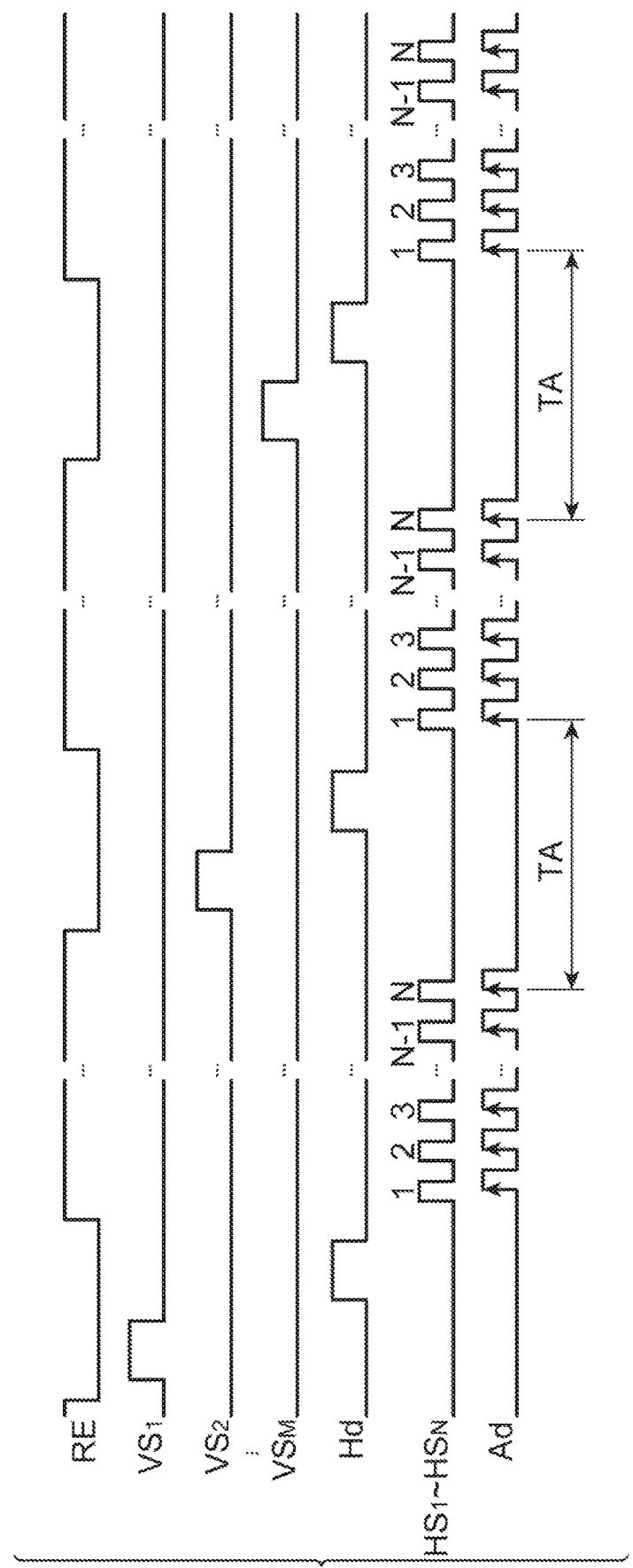
FIG. 9 is a timing chart according to a comparative example.

Effects obtained by the above-described X-ray imaging system 100 and the method of controlling the solid-state imaging device 1A of the present embodiment will be described. When pixel data of the plurality of imaging pixel regions 20A are read out in parallel, the A/D converter 50 may be provided in each imaging pixel region 20A as in the present embodiment. In that case, the following operation is performed in parallel in each imaging pixel region 20A. FIG. 9 is a timing chart according to a comparative example. As shown in FIG. 9, first, when the first row selection control signal $VS_1$ becomes high level, charges generated in the respective pixels $P_{1,\ 1}$ to $P_{1,\ N}$ of the first row are outputted. This output timing is controlled by the vertical shift register unit 30. Next, when the hold control signal Hd becomes high level, a voltage value generated by the integration circuit 42 based on these charges is held by the hold circuit 44. Subsequently, the column selection control signals $HS_1$ to $HS_N$ sequentially become high level, and the voltage value held in the hold circuit 44 is outputted to the output wiring 48 for each column. At this time, each time the voltage value of each column is outputted, the A/D conversion control signal Ad rises. This causes the outputted voltage value to be A/D-converted for each column by the A/D converter 50, and the A/D-converted digital signal is outputted to outside the solid-state imaging device. Such an operation is also performed sequentially for each of second and subsequent rows.

However, when pixel data of the plurality of imaging pixel regions 20A are read out in parallel, pixel values may be discontinuous at a boundary line of the plurality of imaging pixel regions 20A. Furthermore, as shown in FIG. 3, since the alignment direction B2 of the plurality of imaging pixel regions 20A crosses the moving direction B1, the boundary line of the plurality of imaging pixel regions 20A is to extend (e.g., in parallel) along the moving direction B1 of the solid-state imaging device 1A. As a result, pixel data of pixels adjacent to the boundary line is repeatedly integrated, discontinuity is emphasized, and linear noise appears in the boundary line part of a panoramic image after integration.

The inventors have found that a cause of discontinuity of pixel values at the boundary line between the plurality of imaging pixel regions 20A is attributed to the output characteristic of the A/D converter 50. That is, after sequentially converting voltage values from the first column to the N-th column of a certain row into digital signals, the A/D converter 50 sequentially converts voltage values from the first column to the N-th column of the next row into digital signals. At that time, in the A/D converter 50, when starting a conversion of the next row after completing a conversion of the certain row, the output characteristic of the first one or several times of A/D conversion may be different from usual (may become unstable). One reason for this is considered to be a pause period TA that occurs between a completion of a conversion of a certain row and a start of a conversion of the next row, such as a period of holding (hold) of a voltage value of the next row. This is because the output characteristic of the first one or several times of A/D conversion after the pause period TA may become different from usual (become unstable) when such a pause period TA occurs in the A/D converter 50. Therefore, a discontinuity occurs in pixel data between pixel data of a pixel on one side (that is, the pixel $P_{m,\ N}$ of an N-th column) and pixel data of a pixel on the other side (that is, the pixel $P_{m,\ 1}$ of the first column) among pixels located on both sides of the boundary line between the imaging pixel regions 20A. Further, on the other side as well, a discontinuity occurs in pixel data between pixel data of a column in which the A/D conversion becomes unstable and pixel data of a column stably A/D-converted. These discontinuities become linear noise and appear in an integrated image.

Therefore, in the present embodiment, in acquiring at least one frame image, at least any A/D converter 50 executes one or a plurality of times of dummy A/D conversion after converting a voltage value of the m-th row into a digital signal (e.g., after step S3 including the first A/D conversion step), before converting a voltage value of the (m+1)-th row into a digital signal (e.g., before the step S6 including the second A/D conversion step). This allows effective suppression of a change in the output characteristic of the first one or several times of A/D conversion (that is, the A/D conversion of the first column or several columns) after the pause period TA, enabling reduction of discontinuity of pixel values near the boundary line between the plurality of imaging pixel regions 20A. Therefore, according to the present embodiment, linear noise appearing in a panoramic image after integration can be reduced. Meanwhile, according to the findings of the inventors, linear noise in one frame image is small and cannot be visually confirmed, but the linear noise clearly appears when a plurality of frame images are integrated. Therefore, it is sufficient to suppress linear noise as a result of execution of a dummy A/D conversion in "at least one" A/D converter 50 in acquiring "at least one" frame image.

As in the present embodiment, the pause period TA may be provided, after a conversion of the voltage value of the m-th row to a digital signal, before a conversion of the voltage value of the (m+1)-th row into a digital signal. This can provide a period for releasing heat to the A/D converter 50, and suppress temperature rise of the A/D converter 50. Furthermore, an increase in power consumption of the A/D converter 50 can also be suppressed. In a case where the pause period TA is provided, it is possible to suppress heat generation and an increase in power consumption of the A/D converter 50 due to a dummy A/D conversion, by executing a dummy A/D conversion once or several times exclusively immediately before the A/D conversion of an (m+1)-th row as in the present embodiment, instead of continuing to operate the A/D converter 50 during the pause period TA.

As in the present embodiment, in acquiring one frame image, a dummy A/D conversion may be made effective in all of the L pieces of A/D converter 50, or the dummy A/D conversion may be executed in some A/D converters 50 (L1 pieces of A/D converter) among the L pieces of A/D converter 50. For example, a dummy A/D conversion may be executed in the A/D converter 50 of the imaging pixel region 20A adjacent to a boundary line where discontinuity of the pixel value is particularly conspicuous among the boundary lines between the L pieces of imaging pixel region 20A. In addition, for example, in a case where an appearance position of linear noise changes for each frame image, it is preferable that a dummy A/D conversion is executed in all of the L pieces of A/D converter 50. This enables effective reduction of linear noise appearing in a panoramic image after integration.

As in the present embodiment, in acquiring each of a plurality of frame images, a dummy A/D conversion may be executed in at least any A/D converter 50. Thus, executing the dummy A/D conversion in the A/D converter 50 every time each frame image is acquired enables effective reduction of linear noise appearing in a panoramic image after integration.

As in the present embodiment, the L pieces of A/D conversion control wiring 51 that transmit the A/D conversion control signal Ad to the respective L pieces of A/D converter 50 from the second control unit 6b preferably have the same length. This enables effective suppression of deviation of an arrival timing of the A/D conversion control signal Ad between the plurality of A/D converters 50.

As in the present embodiment, the time interval tb (see FIG. 8) between the last dummy A/D conversion among one or a plurality of times of dummy A/D conversion and conversion from a voltage value of the first column of the (m+1)-th row into a digital signal may be equal to the time interval t (see FIG. 8) between conversions of individual columns of an (m+1)-th row from a voltage value to a digital signal. Further, the time interval to (see FIG. 8) between dummy A/D conversions may be equal to the time interval t. At least one of them allows the dummy A/D conversion to simulate the A/D conversion of each column, enabling effective suppression of a change in the output characteristic of the A/D converter 50. In particular, since the A/D conversion in the first column is likely to be unstable, the A/D conversion of the first column can be executed under conditions similar to those of the second and subsequent columns by equalizing the time interval tb and the time interval t described above, enabling more effective suppression of a change in the output characteristic of the A/D converter 50.

(Modification)

Figure 10:
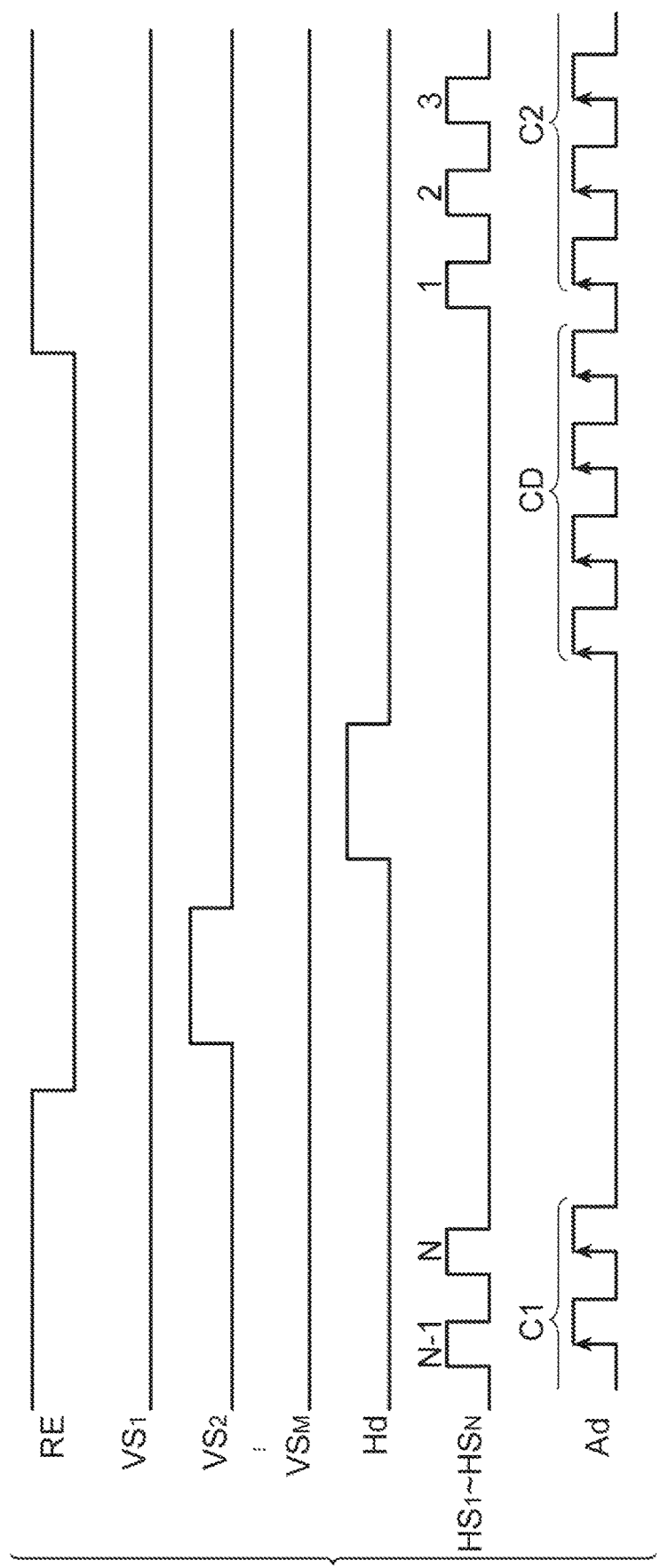
FIG. 10 is a timing chart according to a modification of the present embodiment.

FIG. 10 is a timing chart according to a modification of the above embodiment. In this modification, unlike the above embodiment, a second row selection control signal $VS_2$ becomes high level before a period in which a rise CD of a dummy A/D conversion is provided to the A/D converter 50. At this time, a charge is outputted from each of pixels $P_{2,1}$ to $P_{2,N}$ of a second row, and the charge is converted into a voltage value by an integration circuit 42. Thereafter, a hold control signal Hd becomes high level, and the voltage value corresponding to the charge from each of the pixels $P_{2,1}$ to $P_{2,N}$ of the second row is held in each hold circuit 44. A similar operation is performed for a third to M-th rows. That is, in this modification, the dummy A/D conversion of the A/D converter 50 is executed after the hold circuit 44 takes in the voltage value. This can avoid superimposition of noise caused by the operation of the A/D converter 50 on a voltage value when the voltage value is held by the hold circuit 44. As a result, sharper panoramic images can be created.

Second Embodiment

Figure 11:
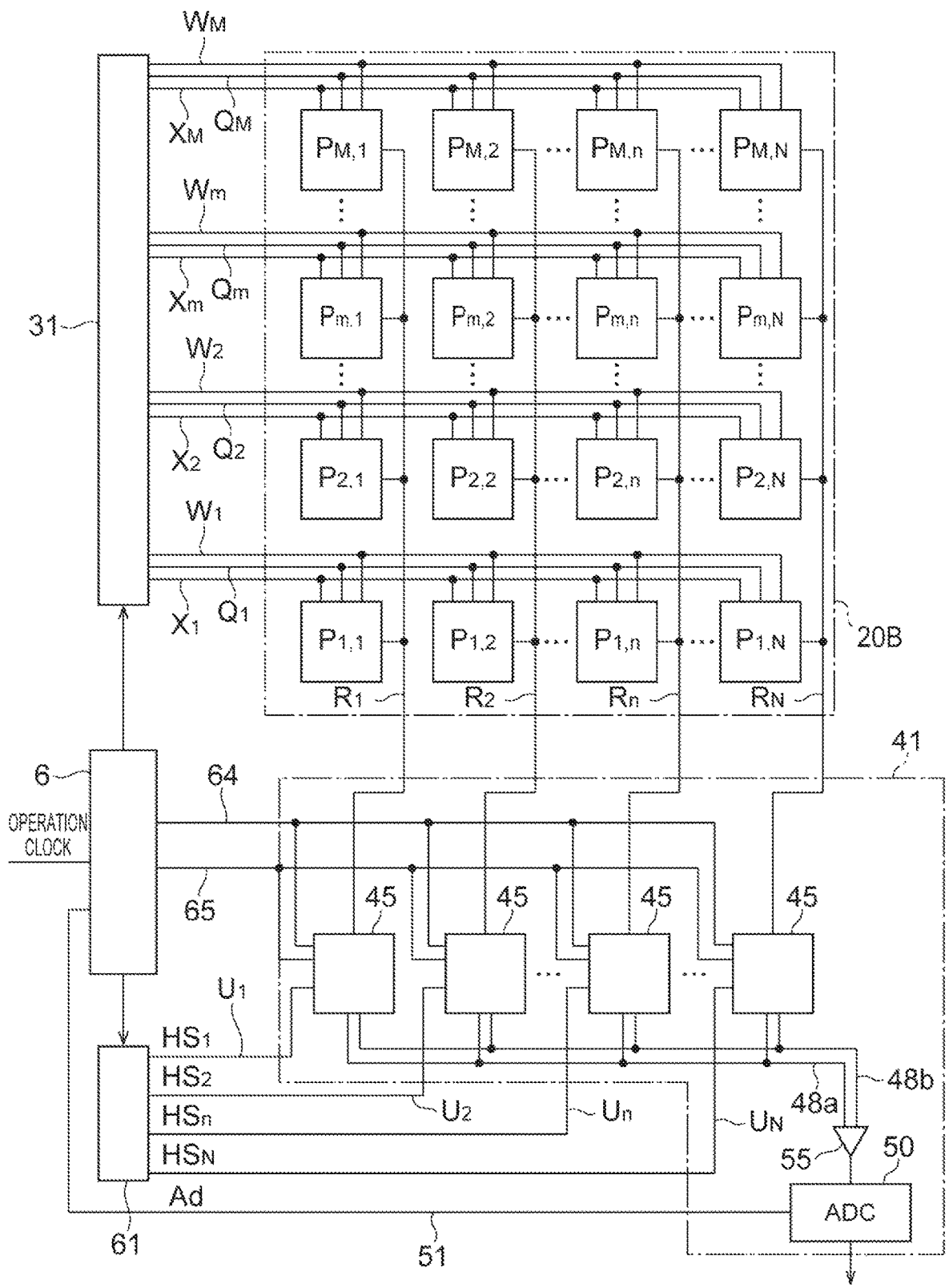
FIG. 11 is a diagram showing a configuration of the imaging pixel region and the signal output unit in an APS solid-state imaging device (an example of the solid-state imaging device according to the present embodiment) applied to the radiation imaging system of FIG. 1.

Next, a radiation imaging system according to a second embodiment will be described. Note that the radiation imaging system according to the second embodiment has the configuration shown in FIG. 1 similarly to the first embodiment, but the second embodiment differs from the first embodiment in that an active pixel sensor (APS) solid-state imaging device is applied as a solid-state imaging device 1A (an example of a solid-state imaging device according to the present embodiment). FIG. 11 is a diagram showing a configuration of an imaging pixel region 20B and a signal output unit 41 in the APS solid-state imaging device. Note that, in order to simplify the description, FIG. 11 shows a configuration example of an APS solid-state imaging device including one imaging pixel region 20B and one signal output unit 41. The imaging pixel region 20B and the signal output unit 41 replace the imaging pixel region 20A and the signal output unit 40 shown in FIG. 3, respectively. Note that, in the example of FIG. 5, the control system 6 is constituted by the plurality of control units including the first control unit 6a and the second control unit 6b configured to operate in accordance with a common operation clock. However, in the example of FIG. 11, a control system 6 is constituted by a single control unit configured to operate in accordance with an operation clock supplied from outside.

The imaging pixel region 20B forms an M-row by N-column matrix with M (an integer of 2 or more)×N (an integer of 2 or more) pieces of pixel $P_{1,1}$ to $P_{M,N}$ arranged two-dimensionally. Each row of the M-row by N-column matrix extends along a longitudinal direction B2 of a light receiving part 2 shown in FIG. 3. Each column extends along a moving direction B1 of the solid-state imaging device 1A shown in FIG. 3. The individual pixels $P_{1,1}$ to $P_{M,N}$ have a common configuration and output a voltage value (analog signal) corresponding to intensity of light incident on a photodiode, to readout wirings $R_1$ to $R_N$. A readout wiring $R_n$ of an n-th column is connected to each output end of M pieces of pixel $P_{1,n}$ to $P_{M,n}$ in the n-th column.

N pieces of pixel $P_{m,1}$ to $P_{m,N}$ of an m-th row are connected to a vertical shift register unit 31 via an m-th row selection wiring $Q_m$, an m-th row reset wiring $W_m$, and an m-th row transfer wiring $X_m$. Note that, the vertical shift register unit 31 is a row selection unit in the present embodiment, and replaces the vertical shift register unit 30 shown in FIG. 3. The vertical shift register unit 31 is electrically connected to the control system 6 and controlled by the control system 6.

The signal output unit 41 has N pieces of hold circuit 45 provided for respective columns. The N pieces of hold circuit 45 have a configuration common to each other. The N pieces of hold circuit 45 respectively have input ends connected to the respective readout wirings $R_1$ to $R_N$, and hold two kinds of voltage values to be sequentially outputted from a pixel $P_{m,n}$ to the readout wiring $R_n$. Then, the held voltage values are outputted from output ends to each of output wirings 48a and 48b. Each of the N pieces of hold circuit 45 is connected to the control system 6 via a first hold wiring 64 and a second hold wiring 65 that are provided in common for the N pieces of hold circuit 45. Further, each of the N pieces of hold circuit 45 is connected to a horizontal shift register unit 61 (column selection unit) via each of a first column selection wiring $U_1$ to an N-th column selection wiring $U_N$. The horizontal shift register unit 61 is electrically connected to the control system 6 and controlled by the control system 6.

The signal output unit 41 further comprises a difference calculation unit 55 and an A/D converter 50. The difference calculation unit 55 is connected to the output end of each hold circuit 45 via the two output wirings 48a and 48b. The difference calculation unit 55 sequentially inputs two kinds of voltage values outputted from each hold circuit 45 to the output wirings 48a and 48b, performs a difference calculation between these two kinds of voltage values, and outputs a voltage value representing the calculation result. The A/D converter 50 converts the voltage value (analog signal) obtained from the difference calculation unit 55 into a digital signal. Note that a configuration and operation of the MD converter 50 are similar to those of the first embodiment.

Figure 12:
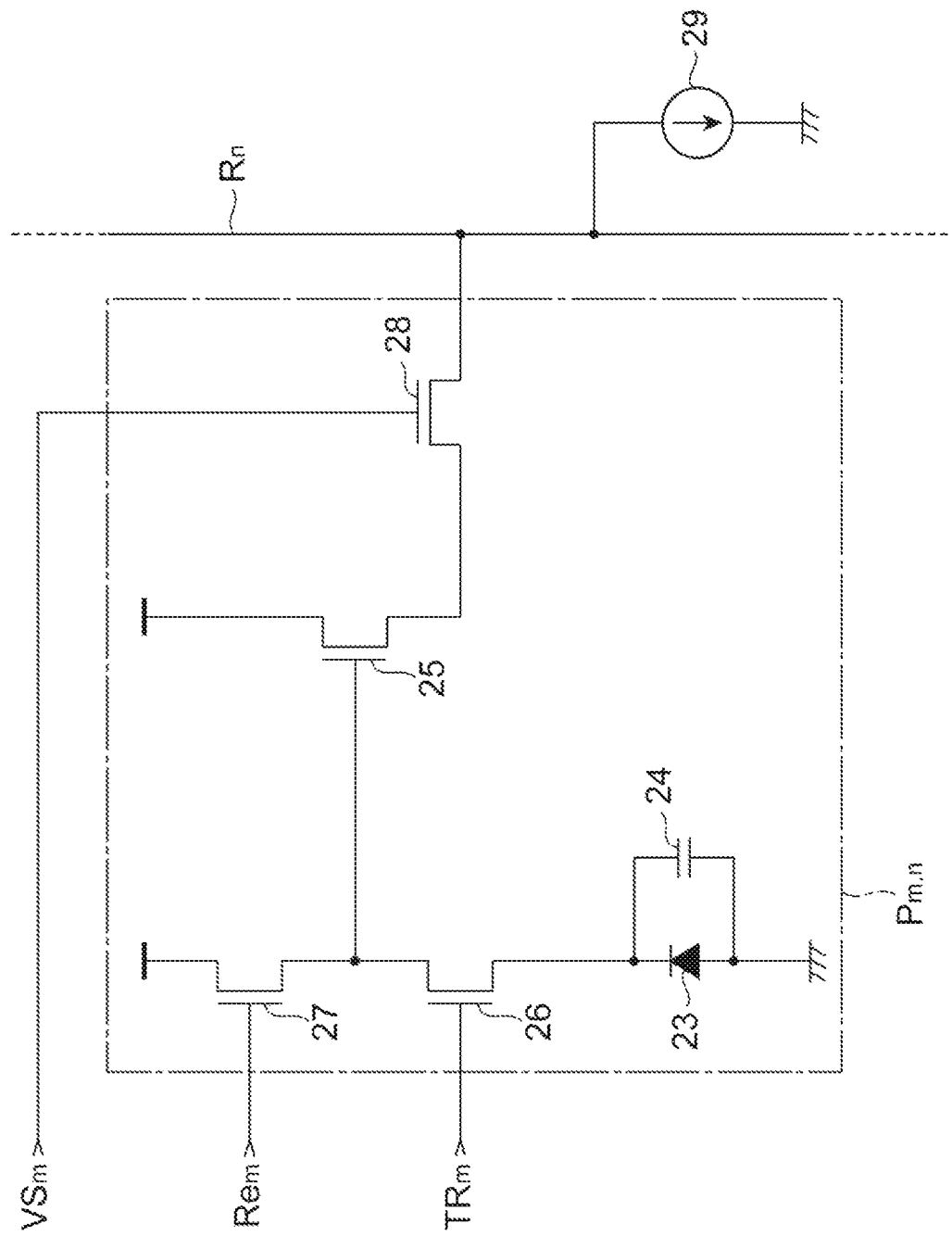
FIG. 12 is a circuit diagram of a pixel in an m-th row, an n-th column.

FIG. 12 is a circuit diagram of the pixel $P_{m,n}$ of the m-th row, the n-th column. The pixel $P_{m,n}$ includes a photodiode 23, a capacitive element 24, an amplifying transistor 25, a transfer transistor 26, a discharge transistor 27, and a selection transistor 28. The photodiode 23 generates an charge of an amount corresponding to intensity of incident light. The capacitive element 24 is connected in parallel to the photodiode 23, and accumulates a charge generated in the photodiode 23. The amplifying transistor 25 outputs a voltage value corresponding to a voltage value inputted to a gate terminal. The transfer transistor 26 inputs a voltage value corresponding to an accumulated charge quantity of the capacitive element 24 to the gate terminal of the amplifying transistor 25. The discharge transistor 27 discharges the charges of the capacitive element 24. The selection transistor 28 selectively outputs the voltage value outputted from the amplifying transistor 25 to the wiring $R_n$. Note that this voltage value is an example of an electric signal generated in the pixel $P_{m,n}$.

A drain terminal of the amplifying transistor 25 is set to a bias potential. A drain terminal of the transfer transistor 26 is connected to the gate terminal of the amplifying transistor 25, and a source terminal of the transfer transistor 26 is connected to a cathode of the photodiode 23 and one terminal of the capacitive element 24. An anode of the photodiode 23 and the opposite terminal of the capacitive element 24 are connected to a ground potential. A source terminal of the discharge transistor 27 is connected to the gate terminal of the amplifying transistor 25, and a drain terminal of the discharge transistor 27 is set to a bias potential. A source terminal of the selection transistor 28 is connected to a source terminal of the amplifying transistor 25, and a drain terminal of the selection transistor 28 is connected to the readout wiring $R_n$. Further, this readout wiring $R_n$ is connected with a constant current source 29. The amplifying transistor 25 and the selection transistor 28 together with the constant current source 29 constitute a source follower circuit.

To a gate terminal of the transfer transistor 26, an m-th row transfer control signal $TR_m$ is inputted via the m-th row transfer wiring) $X_m$ shown in FIG. 11. To a gate terminal of the discharge transistor 27, an m-th row discharge control signal $Re_m$ is inputted via the m-th row reset wiring $W_m$ shown in FIG. 11. In addition, to a gate terminal of the selection transistor 28, an m-th row selection control signal $VS_m$ is inputted via an m-th row selection wiring $Q_m$ shown in FIG. 11. When the m-th row transfer control signal $TR_m$ is at high level and the m-th row discharge control signal $Re_m$ is at low level, the transfer transistor 26 inputs a voltage value corresponding to an accumulated charge quantity of the capacitive element 24 to the gate terminal of the amplifying transistor 25. Whereas, when the m-th row transfer control signal $TR_m$ is at high level and the m-th row discharge control signal $Re_m$ is also at high level, the transfer transistor 26 and the discharge transistor 27 discharge the charges of the capacitive element 24. In addition, when the m-th row selection control signal $VS_m$ is at high level, the selection transistor 28 outputs the voltage value outputted from the amplifying transistor 25 to the readout wiring $R_n$.

In the pixel $P_{m,n}$ thus configured, when the m-th row transfer control signal $TR_m$ becomes low level and the m-th row discharge control signal $Re_m$ becomes high level, charges of the gate terminal of the amplifying transistor 25 are discharged. Further, when the m-th row selection control signal $VS_m$ is at high level, the voltage value (dark signal component) outputted from the amplifying transistor 25 in its initialized state is outputted to the readout wiring $R_n$ via the selection transistor 28. Whereas, when the m-th row discharge control signal $Re_m$ is at low level, and the m-th row transfer control signal $TR_m$ and the m-th row selection control signal $VS_m$ are each at high level, a voltage value corresponding to a charge quantity generated in the photodiode 23 and accumulated in the capacitive element 24 is inputted to the gate terminal of the amplifying transistor 25. A voltage value (bright signal component) outputted from the amplifying transistor 25 in accordance with the input voltage value is outputted to the readout wiring $R_n$ via the selection transistor 28.

Note that the capacitive element 24 configured to store charges is connected in parallel to the photodiode 23 in the circuit shown in FIG. 12, but the capacitive element 24 may be omitted. Moreover, the arrangement of the capacitive element is not limited to this. For example, the capacitive element may be connected between a ground potential line and a node (floating diffusion part) between the transfer transistor 26 and the discharge transistor 27.

In addition, in the circuit shown in FIG. 12, the transfer transistor 26 may be omitted. In this case as well, the capacitive element 24 may be connected in parallel to the photodiode 23, or the capacitive element 24 may be omitted.

Figure 13:
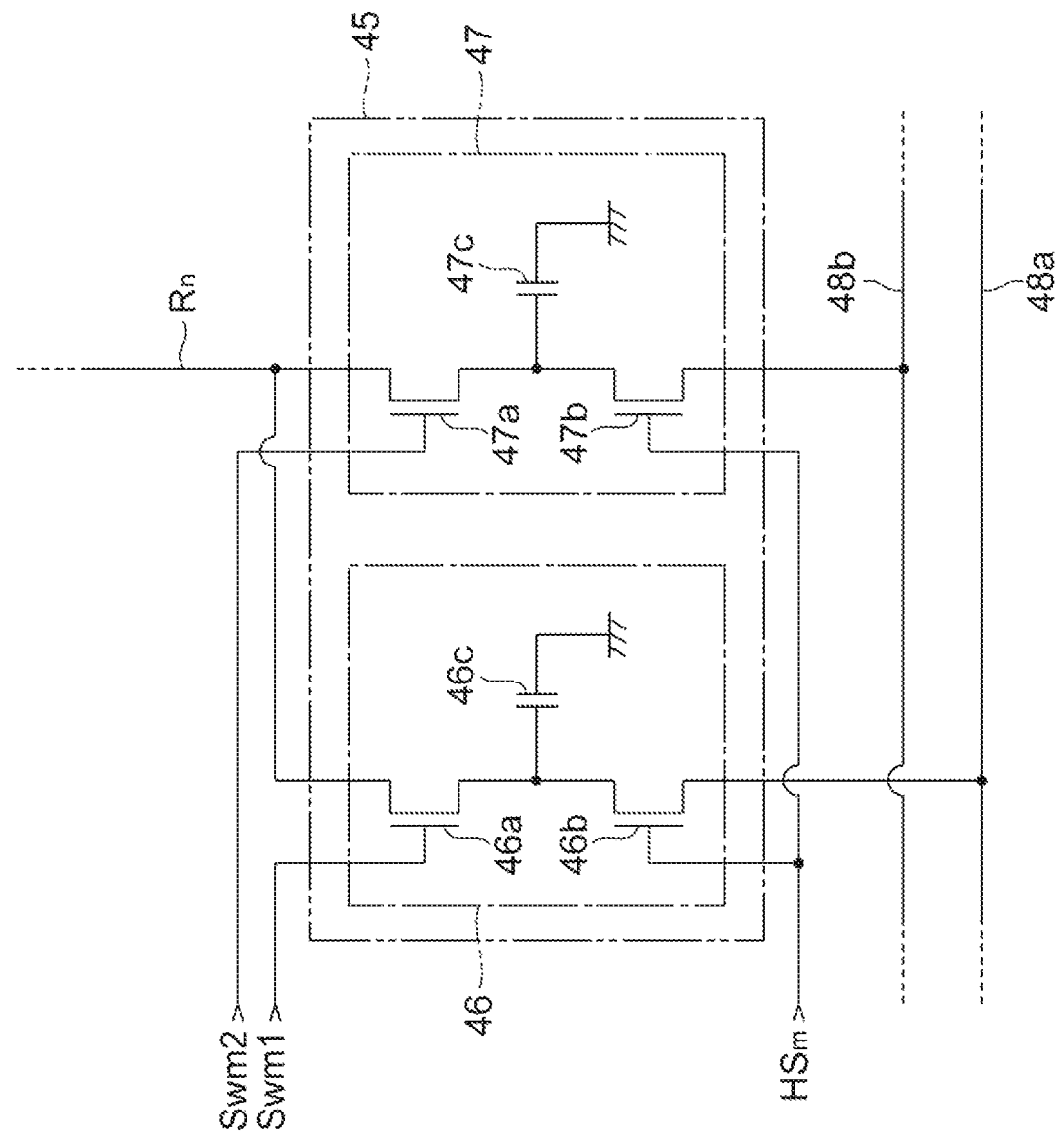
FIG. 13 is a circuit diagram of the hold circuit.

FIG. 13 is a circuit diagram of each hold circuit 45. As shown in FIG. 13, each hold circuit 45 includes a first holding part 46 and a second holding part 47. The first holding part 46 and the second holding part 47 each have a configuration similar to each other. Further, the first holding part 46 and the second holding part 47 can each input and hold voltage values sequentially outputted from the selection transistors 28 of the respective M pieces of pixel $P_{1,n}$ to $P_{M,n}$ existing in the n-th column, and can also output the held voltage values.

The first holding part 46 includes a transistor 46a, a transistor 46b, and a capacitive element 46c. One end of the capacitive element 46c is at a ground potential, and the other end of the capacitive element 46c is connected to each of a drain terminal of the transistor 46a and a source terminal of the transistor 46b. A source terminal of the transistor 46a is connected to the selection transistor 28 of the pixel $P_{m,n}$, via the readout wiring $R_n$. A drain terminal of the transistor 46b is connected to the output wiring 48a. The first holding part 46 thus configured causes the capacitive element 46c to hold a voltage value outputted from the pixel $P_{m,n}$ connected via the readout wiring $R_n$, when a first input control signal Swm1 inputted to a gate terminal of the transistor 46a via the first hold wiring 64 shown in FIG. 11 is at high level. Further, when an m-th column selection control signal $HS_m$ inputted to a gate terminal of the transistor 46b via an m-th column selection wiring $U_m$ shown in FIG. 11 is at high level, the first holding part 46 outputs the voltage value held in the capacitive element 46c to the output wiring 48a.

The second holding part 47 includes a transistor 47a, a transistor 47b, and a capacitive element 47c. One end of the capacitive element 47c is set to a ground potential, and the other end of the capacitive element 47c is connected to each of a drain terminal of the transistor 47a and a source terminal of the transistor 47b. A source terminal of the transistor 47a is connected to the selection transistor 28 of the pixel $P_{m,n}$ via the readout wiring $R_n$. A drain terminal of the transistor 47b is connected to the output wiring 48b. The second holding part 47 thus configured causes the capacitive element 47c to hold a voltage value outputted from the pixel $P_{m,n}$ connected via the readout wiring $R_n$, when a second input control signal Swm2 inputted to a gate terminal of the transistor 47a via the second hold wiring 65 shown in FIG. 11 is at high level. In addition, the second holding part 47 outputs the voltage value held in the capacitive element 47c to the output wiring 48b when the m-th column selection control signal $HS_m$ inputted to a gate terminal of the transistor 47b via the m-th column selection wiring $U_m$ shown in FIG. 11 is at high level.

The first holding part 46 and the second holding part 47 respectively operate at timings different from each other. For example, the first holding part 46 holds a voltage value (dark signal component) outputted from the amplifying transistor 25, when the m-th row transfer control signal $TR_m$ is at low level and the m-th row discharge control signal $Re_m$ and the m-th row selection control signal $VS_m$ are each at high level, in the pixel $P_{m,n}$ connected via the readout wiring $R_n$. Whereas, the second holding part 47 holds a voltage value (bright signal component) outputted from the amplifying transistor 25, when the m-th row discharge control signal $Re_m$ is at low level and the m-th row transfer control signal $TR_m$ and the m-th row selection control signal $VS_m$ are each at high level, in the pixel $P_{m,n}$ connected via the readout wiring $R_n$.

Figure 14:
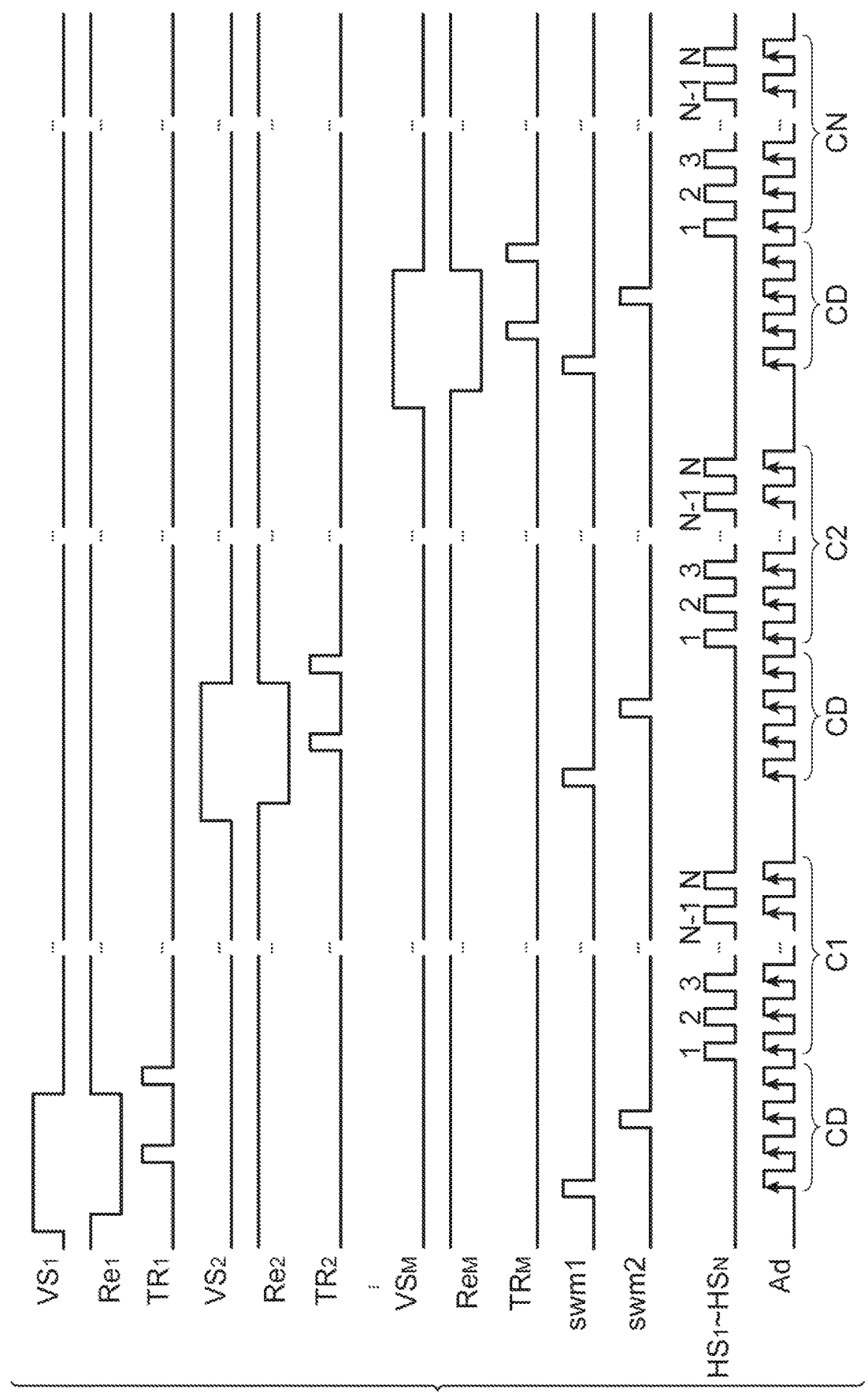
FIG. 14 is a timing chart of individual signals inputted to the imaging pixel region and the signal output unit.

FIG. 14 is a timing chart of individual signals inputted to the imaging pixel region 20B and the signal output unit 41. FIG. 14 shows, in order from the top, each of the first row selection control signal $VS_1$, the first row discharge control signal $Re_1$, the first row transfer control signal $TR_1$, the second row selection control signal $VS_2$, the second row discharge control signal $Re_2$, the second row transfer control signal $TR_2$, the M-th row selection control signal $VS_M$, an M-th row discharge control signal $Re_M$, an M-th row transfer control signal $TR_M$, the first input control signal Swm1, the second input control signal Swm2, the first column selection control signal $HS_1$ to the N-th column selection control signal $HS_N$, and an A/D conversion control signal Ad. Note that, in a period during which a voltage value corresponding to intensity of incident light to the pixel $P_{m,n}$ is outputted from the imaging pixel region 20B, the m-th row selection control signal $VS_m$ inputted to the gate terminal of the selection transistor 28 of the pixel $P_{m,n}$ is at high level.

First, when the first row transfer control signal $TR_1$ is at low level and the first row discharge control signal $Re_1$ is at high level, the first input control signal Swm1 and the second input control signal Swm2 are at low level. Next, the first row discharge control signal $Re_1$ turns to low level. Thereafter, the first input control signal Swm1 turns to high level, and then turns to low level. During a period where the first input control signal Swm1 is at high level, a voltage value (dark signal component) outputted from the amplifying transistor 25 of the pixel $P_{1,n}$ is held in the capacitive element 46c of the first holding part 46.

Subsequently, the first row transfer control signal $TR_1$ turns to high level, and then turns to low level. As a result, a voltage value corresponding to a charge quantity generated in the photodiode 23 and accumulated in the capacitive element 24 is inputted to the gate terminal of the amplifying transistor 25. Subsequently, the second input control signal Swm2 turns to high level, and then turns to low level. During a period where the second input control signal Swm2 is at high level, a voltage value (bright signal component) outputted from the amplifying transistor 25 of the pixel $P_{1,n}$ is held in the capacitive element 47c of the second holding part 47. Then, the first row discharge control signal $Re_1$ turns to high level. As a result, charges of the capacitive element 24 are discharged. Thereafter, the first row transfer control signal turns to high level, and then turns to low level. This causes the capacitive element 24 to be reset.

Subsequently, the voltage values held in the capacitive elements 46c and 47c are outputted to the output wirings 48a and 48b for each column. Specifically, the horizontal shift register unit 61 sequentially sets the first column selection control signal $HS_1$ to the N-th column selection control signal $HS_N$ to high level. This causes the voltage value held in the capacitive element 46c to be sequentially outputted to the output wiring 48a. Further, the voltage values held in the capacitive element 47c are sequentially outputted to the output wiring 48b. These voltage values are inputted to the difference calculation unit 55. The difference calculation unit 55 calculates a difference between the inputted voltage values, and outputs a voltage value representing the calculation result. This voltage value is an analog signal corresponding to intensity of light incident on the photodiode 23 of the pixel $P_{m,n}$, and has an excellent S/N ratio by removing the dark signal component.

Further, at this time, the voltage value outputted from the difference calculation unit 55 is converted into a digital signal by the A/D converter 50. Specifically, every time the horizontal shift register unit 61 sets each column selection control signal $HS_n$ to high level, the control system 6 raises the A/D conversion control signal Ad from low level to high level. This raising operation is performed immediately after each column selection control signal $HS_n$ is set to high level.

This causes each voltage value of each column, which is an analog signal outputted from the difference calculation unit 55, to be converted into a digital signal. These digital signals are outputted to outside the solid-state imaging device 1A as pixel data of a first row of one frame image.

Thereafter, for a second row to an M-th row, a digital signal corresponding to intensity of light incident on the photodiode 23 of the pixel $P_{m, n}$ is generated by an operation similar to that for the first row. In this way, reading of one frame image from the L pieces of imaging pixel region 20B is completed. The solid-state imaging device acquires a plurality of frame images by repeatedly performing such an operation while moving. Then, one panoramic image is created by integrating the plurality of frame images while the frame images are shifted by a distance corresponding to a moving speed of the solid-state imaging device, along an axial direction corresponding to a moving direction of the solid-state imaging device.

Here, in the present embodiment as well, one or a plurality of times of dummy A/D conversion are executed, after the A/D converter 50 converts a voltage value of the m-th row into a digital signal before converting a voltage value of the (m+1)-th row into a digital signal. For example, after providing an A/D conversion control signal Ad with a rise (symbol C1 in FIG. 14) corresponding to the first to M-th columns of the first row, before providing the A/D conversion control signal Ad with a rise (symbol C2 in FIG. 14) corresponding to the first to M-th columns of the second row, the control system 6 provides the A/D conversion control signal Ad with a rise (symbol CD in FIG. 14) of a dummy A/D conversion. This rise of a dummy A/D conversion may be once or a plurality of times (FIG. 14 illustrates a case of four times). The control system 6 also performs similar processing for third and subsequent rows. That is, after providing the A/D conversion control signal Ad with a rise corresponding to the first to M-th columns of the m-th row, before providing the A/D conversion control signal Ad with a rise corresponding to the first to M-th columns of the (m+1)-th row, the control system 6 provides the A/D conversion control signal Ad with a rise CD of a dummy A/D conversion.

As in the present embodiment, the solid-state imaging device 1A of the radiation imaging system (X-ray imaging system 100) is not limited to the PPS solid-state imaging device (the first embodiment), and the solid-state imaging device 1A is also applicable to the APS solid-state imaging device (the second embodiment). Even in that case, a change in the output characteristic of the first A/D conversion after a pause period can be suppressed, and discontinuity of pixel values at a boundary line of the plurality of imaging pixel regions 20B can be effectively reduced. Therefore, linear noise appearing in a panoramic image after integration can be reduced.

Further, in the present embodiment as well, as shown in FIG. 10, a dummy A/D conversion of the A/D converter 50 may be performed after the hold circuit 45 takes in the voltage value. This can avoid superimposition of noise caused by the operation of the A/D converter 50 on a voltage value when the voltage value is held by the hold circuit 45, enabling creation of a sharper panoramic image.

The radiation imaging system and the method of controlling the solid-state imaging device according to the present embodiment are not limited to the above-described embodiments, and various other modifications are possible. For example, the above-described embodiments and modification may be combined with each other in accordance with necessary purposes and effects. Specifically, the above embodiment exemplifies the case where the solid-state imaging device moves, but it is sufficient to relatively move a position of the solid-state imaging device with respect to the subject. For example, the position of the solid-state imaging device may be fixed and the subject may be moved. Such a configuration is useful, for example, in an X-ray inspection device.

In the above embodiment, X-rays are shown as an example of radiation, but the radiation imaging system according to the present embodiment can also be applied to a system for imaging radiation other than X-rays. The above embodiment exemplifies the configuration in which the scintillator is provided on the light receiving part, but above embodiment can also be applied to a radiation imaging system having a solid-state imaging device (e.g., each pixel includes CdTe) of a type directly converting radiation into an electric signal without using a scintillator. Further, the present embodiment is also effective for a solid-state imaging device in which a direct conversion element such as CdTe is combined with a reading circuit, such as a CMOS-ASIC or a TFT substrate.

The above embodiment exemplifies the case of dental panoramic imaging, but the embodiment can also be applied to other imaging modes (e.g., CT imaging or cephalometric imaging) as long as it is a mode of integrating a plurality of frame images obtained by moving the solid-state imaging device. In addition, in the present embodiment, the longitudinal direction of the solid-state imaging device does not need to be strictly orthogonal to the moving direction, and these directions may be slightly inclined. In the above embodiment, a voltage value based on an electric signal outputted from each pixel is temporarily held by the hold circuit, but such a hold circuit may be omitted.

In the above embodiment, the CMOS solid-state imaging device is applied, but a TFT solid-state imaging device made by amorphous silicon, for example, is also applicable. In addition, the present embodiment is also effective in a case where a plurality of imaging elements are tiled and used as one solid-state imaging device.

In the above embodiment, the shift register is used as the row selection unit and the column selection unit, but the row selection unit and the column selection unit are not limited to this, and other circuits such as a decoder may be used, for example. In the above embodiment, a pause period is provided between the A/D conversion of the m-th row and the A/D conversion of the (m+1)-th row, and a dummy A/D conversion is executed during the pause period. However, the present embodiment can also be applied to a case where no pause period is provided. Even in such a case, the effect of the above embodiment can be obtained by executing the dummy A/D conversion between the A/D conversion of the m-th row and the A/D conversion of the (m+1)-th row.

As a readout method of the solid-state imaging elements, there is a column AD system in which, for example, an A/D converter is provided for each column. In such a system, even if there is a pause period, noise is averaged since the A/D conversion is performed under the same conditions in all columns. The present embodiment is to solve the problem caused by the fact that there are a plurality of imaging pixel regions, each imaging pixel region includes a plurality of columns, and an A/D converter is provided in each imaging pixel region.

In the above embodiment, the radiation imaging system including the solid-state imaging device and the method of controlling the solid-state imaging device have been described, but the features of the present embodiment may be embodied in the solid-state imaging device itself. That is, the solid-state imaging device according to the present embodiment is a device for capturing an image formed by radiation emitted from a radiation source and transmitted through a subject, and comprises at least a light receiving part, a row selection unit, a column selection unit, L (an integer of 2 or more) pieces of A/D converter, and a control system. The light receiving part has L pieces of imaging pixel region arranged in a direction crossing a predetermined direction. Each imaging pixel region includes M (an integer of 2 or more)×N (an integer of 2 or more) pieces of pixel arranged two-dimensionally, and these M×N pieces of pixel form an M-row by N-column matrix. Further, in each imaging pixel region, each column of the M-row by N-column matrix extends along a predetermined direction. The row selection unit outputs an electric signal corresponding to a charge quantity generated in a plurality of pixels for each row. The column selection unit outputs an analog signal based on the electric signal outputted for each row to an output wiring for each column. The L pieces of A/D converter are respectively provided corresponding to the L pieces of imaging pixel region. Each of the L pieces of A/D converter converts an analog signal transmitted via the output wiring into a digital signal to become a frame image. During a period of acquiring at least one frame image, the control system controls at least any A/D converter selected from among the L pieces of A/D converter such that the selected A/D converter executes one or a plurality of times of dummy A/D conversion after converting an analog signal of an m-th row (m is an integer of 1 or more and M or less) into a digital signal, before converting an analog signal of an (m+1)-th row into a digital signal.

According to this solid-state imaging device, similarly to the above embodiment, a change in the output characteristic of the first one or several times of A/D conversion (that is, the A/D conversion in the first column or several columns) of each row is suppressed. Further, for example, the solid-state imaging device that repeatedly captures images during movement while relatively moving with respect to a subject along a predetermined direction can be applied to an application for generating an image by integrating a plurality of frame images obtained while shifting along an axial direction corresponding to a moving direction of the solid-state imaging device by a distance corresponding to a moving speed of the solid-state imaging device. In this case, since discontinuity of pixel values near a boundary line of the plurality of imaging pixel regions can be reduced, linear noise appearing in an integrated image is reduced.

In addition, the solid-state imaging device may further comprise a hold circuit configured to hold an analog signal before being outputted to the output wiring for each column, and the A/D converter may execute a dummy A/D conversion after the hold circuit takes in the analog signal. This can avoid superimposition of noise caused by the operation of the A/D converter on an analog signal when the analog signal is held by the hold circuit.

In the solid-state imaging device described above, during a period of acquiring one frame image, a dummy A/D conversion may be executed in all of the L pieces of A/D converter, or a dummy A/D conversion may be executed in some A/D converters among the L pieces of A/D converter. The effects of the above-described radiation imaging system can also be suitably exhibited by any of these aspects.

In the solid-state imaging device described above, a dummy A/D conversion may be executed by at least any A/D converter for each period of acquiring each of the plurality of frame images. Thus, executing the dummy A/D conversion in the A/D converter every time each frame image is acquired enables effective reduction of linear noise appearing in an image.

The solid-state imaging device described above may further comprise a control system configured to output a control signal for controlling an A/D conversion timing to the L pieces of A/D converter, and lengths of L pieces of wiring configured to respectively transmit control signals to the L pieces of A/D converter from the control system may be equal to each other. This allows effective suppression of deviation in an arrival timing of the control signal between the plurality of A/D converters.

Further, in the solid-state imaging device, a time interval from an A/D conversion of the (m+1)-th row to an A/D conversion of an adjacent column may be equal to a time interval between the last dummy A/D conversion among one or a plurality of times of dummy A/D conversion executed before the A/D conversion of the (in +1)-th row and an A/D conversion of a first column of the (m+1)-th row. This allows the dummy A/D conversion to simulate the A/D conversion of each column, enabling effective suppression of a change in the output characteristic of the A/D converter.

REFERENCE SIGNS LIST

1A . . . solid-state imaging device; 2 . . . light receiving part; 6 . . . control system; 6a . . . first control unit; 6b . . . second control unit; 20A, 20B . . . imaging pixel region; 21 . . . transistor; 22, 23 . . . photodiode; 24 . . . capacitive element; 25 . . . amplifying transistor; 26 . . . transfer transistor; 27 . . . discharge transistor; 28 . . . selection transistor; 29 . . . constant current source; 30, 31 . . . vertical shift register unit; 40, 41 . . . signal output unit; 42 . . . integration circuit; 44, 45 . . . hold circuit; 46 . . . first holding part; 47 . . . second holding part; 48, 48a, 48b . . . output wiring; 49 . . . amplifier; 50 . . . A/D converter; 51 . . . A/D conversion control wiring; 55 . . . difference calculation unit; 61 . . . horizontal shift register unit; 62 . . . hold wiring; 63 . . . reset wiring; 64 . . . first hold wiring; 65 . . . second hold wiring; 100 . . . X-ray imaging system; 104 . . . swing arm; 106 . . . X-ray source; 200 . . . image generation unit; A . . . subject; B1 . . . moving direction; B2 . . . longitudinal direction; $P_{1,n}$ . . . pixel; and Q1 to Q4 . . . frame image.

The invention claimed is:

1. A solid-state imaging device which has L pieces of imaging pixel regions, L being an integer of 2 or more, arranged along a first direction and captures a radiation image of a subject irradiated with radiation from a radiation source, the solid-state imaging device comprising:

a light receiving part having the L pieces of imaging pixel region, wherein each of the L pieces of imaging pixel region includes M×N pieces of pixel arranged two-dimensionally, M being an integer of 2 or more and N being an integer of 2 or more, and pixels constituting each column of an M-row by N-column matrix corresponding to a two-dimensional array of the M×N pieces of pixel extend along a second direction crossing the first direction;

a row selection unit configured to output an electric signal corresponding to a charge quantity generated in each pixel constituting any one row of the M-row by N-column matrix;

a column selection unit configured to output an analog signal based on the electric signal outputted from each pixel constituting a row selected by the row selection unit, to an output wiring for each column of the M-row by N-column matrix;

L pieces of A/D converter respectively provided corresponding to the L pieces of imaging pixel region, and configured to convert an analog signal transmitted via the output wiring into a digital signal constituting a frame image; and a control system configured to output, during a period of acquiring at least one specific frame image among a plurality of frame images obtained by repeatedly capturing a radiation image of the subject, an A/D conversion control signal once or more times for causing at least any A/D converter selected from among the L pieces of A/D converter to execute a dummy A/D conversion after the selected A/D converter converts an analog signal from a pixel constituting an m-th row out of the M-row by N-column matrix into a digital signal and before converting an analog signal from a pixel constituting an (m+1)-th row into a digital signal, the m being an integer of 1 or more and M or less.

2. The solid-state imaging device according to claim 1, further comprising a hold circuit arranged between the light receiving part and the output wiring, and configured to hold the analog signal before being outputted to the output wiring for each column of the M-row by N-column matrix, wherein
after the hold circuit takes in the analog signal, the control system outputs an A/D conversion control signal for causing the selected A/D converter to execute the dummy A/D conversion.

3. The solid-state imaging device according to claim 1, wherein the control system outputs an A/D conversion control signal for causing each of all the L pieces of A/D converter to execute the dummy A/D conversion during a period of acquiring the one specific frame image.

4. The solid-state imaging device according to claim 1, wherein during a period of acquiring the one specific frame image, the control system outputs an A/D conversion control signal for causing each of L1 pieces of A/D converter among the L pieces of A/D converter to execute the dummy A/D conversion, the L1 being 2 or more and less than L.

5. The solid-state imaging device according to claim 1, wherein for each period of acquiring each of the plurality of frame images, the control system outputs an A/D conversion control signal for causing the selected A/D converter to execute the dummy A/D conversion.

6. The solid-state imaging device according to claim 1, further comprising L pieces of A/D conversion control wiring configured to electrically independently connect the control system and the L pieces of A/D converter, respectively, wherein
the L pieces of A/D conversion control wiring each have a length equal to each other.

7. The solid-state imaging device according to claim 1, wherein a time interval of an A/D conversion executed for each column of the (m+1)-th row is equal to a time interval from a last dummy A/D conversion to an A/D conversion of a first column of the (m+1)-th row among dummy A/D conversions executed during a period from an A/D conversion of a last column of the m-th row to an A/D conversion of a first column of the (m+1)-th row.

8. The solid-state imaging device according to claim 1, wherein the control system gives an instruction on each operation timing of row selection by a row selection unit and column selection by the column selection unit.

9. A radiation imaging system comprising:
the solid-state imaging device according to claim 1;
a moving mechanism configured to relatively move a position of the solid-state imaging device with respect to the subject along the second direction; and
an image generation unit configured to generate an image by integrating each of the plurality of frame images obtained while moving a relative position of the solid-state imaging device with respect to the subject along the second direction, while shifting the frame images along an axial direction corresponding to the second direction by a distance corresponding to a moving speed of a relative position of the solid-state imaging device.

10. A method of controlling the solid-state imaging device according to claim 1, the method comprising:
a first A/D conversion step of converting an analog signal based on an electric signal from a pixel constituting an m-th row out of the M-row by N-column matrix into a digital signal for each column of the m-th row in the L pieces of A/D converter, the m being an integer of 1 or more and M or less;
a second A/D conversion step of converting an analog signal based on an electric signal from a pixel constituting an (m+1)-th row of the M-row by N-column matrix into a digital signal for each column of the (m+1)-th row in the L pieces of A/D converter; and
a dummy A/D conversion step of causing at least any A/D converter among the L pieces of A/D converter to execute a dummy A/D conversion once or more times between the first A/D conversion step and the second A/D conversion step, during a period of acquiring at least any frame image among the plurality of frame images.

* * * * *